(12) United States Patent
Takemoto et al.

(10) Patent No.: US 9,955,857 B2
(45) Date of Patent: May 1, 2018

(54) ENDOSCOPE DEVICE

(71) Applicant: OLYMPUS CORPORATION, Tokyo (JP)

(72) Inventors: Shotaro Takemoto, Tokyo (JP); Madoka Ito, Tokyo (JP); Tetsuyuki Sakamoto, Tokyo (JP); Kazuo Banju, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/336,928

(22) Filed: Oct. 28, 2016

(65) Prior Publication Data

US 2017/0042412 A1 Feb. 16, 2017

Related U.S. Application Data

(63) Continuation of application No. PCT/JP2015/064809, filed on May 22, 2015.

(30) Foreign Application Priority Data

Jun. 19, 2014 (JP) ................................. 2014-126564

(51) Int. Cl.
*A61B 1/00* (2006.01)
*A61B 1/01* (2006.01)
(Continued)

(52) U.S. Cl.
CPC .................. *A61B 1/01* (2013.01); *A61B 1/00* (2013.01); *A61B 1/00006* (2013.01);
(Continued)

(58) Field of Classification Search
CPC ........................... A61B 1/0051; A61B 1/0055
(Continued)

(56) References Cited

U.S. PATENT DOCUMENTS

2002/0058858 A1 5/2002 Ogura et al.
2012/0182409 A1* 7/2012 Moriyama ......... A61B 1/00006
348/65
2013/0109919 A1* 5/2013 Sugiyama ............ A61B 1/0052
600/117

FOREIGN PATENT DOCUMENTS

EP 2484268 A1 8/2012
JP H06-154154 A 6/1994
(Continued)

OTHER PUBLICATIONS

Japanese Office Action dated Mar. 22, 2016 issued in 2016-500008.
(Continued)

*Primary Examiner* — Matthew J Kasztejna
*Assistant Examiner* — Rynae Boler
(74) *Attorney, Agent, or Firm* — Scully, Scott, Murphy & Presser, P.C.

(57) ABSTRACT

An endoscope device includes a flexible insertion portion; a flexible tube portion; a first bending portion; a second bending portion; an observation portion; a first drive portion bending the first bending portion; a second drive portion bending the second bending portion; a position detection portion detecting a position of a rigid distal end portion of a medical instrument; first and second bending detection portions detecting radii of curvature of axes of channels formed in the first and second bending portions and directions in which the channels are bent when an input signal generated by the position detection portion is received, respectively; and a control portion configured to control generating a second drive signal driving the second drive portion based on a first drive signal driving the first drive portion, and sending the second drive signal to the second drive portion while sending the first drive signal.

6 Claims, 21 Drawing Sheets

(51) Int. Cl.
*G02B 23/24* (2006.01)
*A61B 1/005* (2006.01)
*A61B 1/008* (2006.01)
*A61B 1/018* (2006.01)
*A61B 5/06* (2006.01)
*H04N 5/225* (2006.01)

(52) U.S. Cl.
CPC ............ *A61B 1/008* (2013.01); *A61B 1/0016* (2013.01); *A61B 1/0055* (2013.01); *A61B 1/0057* (2013.01); *A61B 1/018* (2013.01); *A61B 5/065* (2013.01); *G02B 23/24* (2013.01); *G02B 23/2484* (2013.01); *H04N 5/2256* (2013.01); *H04N 2005/2255* (2013.01)

(58) Field of Classification Search
USPC .......................................... 600/104, 145, 146
See application file for complete search history.

(56) References Cited

FOREIGN PATENT DOCUMENTS

| | | |
|---|---|---|
| JP | 2002-177202 A | 6/2002 |
| JP | 2009-160211 A | 7/2009 |
| JP | 2013-126506 A | 6/2013 |
| WO | WO 2011/040104 A1 | 4/2011 |
| WO | WO 2012/014532 A1 | 2/2012 |

OTHER PUBLICATIONS

International Search Report dated Aug. 11, 2015 issued in PCT/JP2015/064809.

* cited by examiner

ENDOSCOPE DEVICE

This application is a continuation application based on a PCT International Application No. PCT/JP2015/064809, filed on May 22, 2015, whose priority is claimed on Japanese Patent Application No. 2014-126564, filed on Jun. 19, 2014. The contents of both the PCT International Application and the Japanese Patent Application are incorporated herein by reference.

BACKGROUND OF THE INVENTION

Field of the Invention

The present invention relates to an endoscope device that is used to observe a treatment target.

Description of Related Art

In the past, an endoscope device has been used to observe a treatment target in a body cavity or the like and to perform a treatment. For example, a device disclosed in PCT International Publication No. WO2012/014532 is known as this kind of endoscope device.

The endoscope device disclosed in PCT International Publication No. WO2012/014532 includes an endoscope that images a treatment target, a control unit that is detachably connected to the endoscope, and a monitor that is connected to the control unit and displays the treatment target imaged by the endoscope.

The endoscope includes an insertion portion that is elongated and flexible and an operation portion that is disposed at a proximal end portion of the insertion portion. The insertion portion includes a rigid distal end portion, a bending portion, and a flexible tube portion that are arranged in an order from a distal end portion side toward a proximal end portion side.

The rigid distal end portion includes an imaging surface of an imaging unit (an observation portion) and a distal opening portion of a treatment tool-insertion channel (a channel).

The bending portion includes a first bending portion, a second bending portion, and a third bending portion that are arranged in an order from the rigid distal end portion side toward the flexible tube portion side. For example, the first bending portion is bent vertically and laterally. The second bending portion is bent vertically, and the third bending portion is bent laterally.

An operation portion main body of the operation portion includes a first bending operation portion that bends the first bending portion. The operation portion main body is provided with a second bending operation portion that bends the second bending portion. First and second bending operation mechanisms, which include pulleys and the like, are connected to the first and second bending operation portions, respectively.

The operation portion main body is provided with a third bending operation portion, a drive portion, and a lateral third bending operation mechanism. The third bending operation portion operates to bend the third bending portion. The drive portion has a drive force that allows the third bending portion to be bent laterally by electric power, and is disposed in the operation portion main body. The drive portion is, for example, a motor. The drive force of the drive portion is transmitted to the third bending operation mechanism.

The control unit includes a bending angle calculation portion and a control portion. The bending angle calculation portion calculates bending angles of the first bending portion, the second bending portion, and the third bending portion. The control portion controls the drive portion based on the calculation result calculated by the bending angle calculation portion so that the third bending portion is bent and a distal end portion of the insertion portion approaches a target point (a treatment target).

When a control operation portion included in the operation portion main body is operated, the control portion sets a point, which is distant from the imaging surface of the imaging unit toward, for example, the inside of the body cavity by a desired distance, as a target point. At this time, the control portion calculates the position of the target point.

When the third bending portion is bent, the control portion determines whether or not the target point is positioned in an image surface (an imaging angle of view) imaged by the imaging surface, based on the calculation result (a bending angle) calculated by the bending angle calculation portion.

If the target point is positioned in the image surface, the control portion controls the drive portion based on the calculation result calculated by the bending angle calculation portion so that the third bending portion is bent and the distal end portion of the insertion portion approaches the target point.

When the drive portion is controlled by the control portion so that the target point continues to be positioned in the image surface, the target point continues to be displayed on the monitor. Accordingly, an operator can easily operate the endoscope device.

SUMMARY OF THE INVENTION

According to a first aspect of the invention, an endoscope device includes: a flexible insertion portion in which a channel, into which a medical instrument is capable of being inserted, is formed; a flexible tube portion that is disposed at a proximal end portion of the insertion portion; a first bending portion that is disposed more distal than the flexible tube portion of the insertion portion and is bendable with respect to a distal end portion of the flexible tube portion; a second bending portion that is disposed more distal than the first bending portion of the insertion portion and is bendable with respect to a distal end portion of the first bending portion; an observation portion that is disposed more distal than the second bending portion of the insertion portion and configured to acquire an image on the front of the insertion portion; a first drive portion that is configured to bend the first bending portion with respect to the distal end portion of the flexible tube portion by advancing or retracting a first operation wire which is connected to the first bending portion; a second drive portion that is configured to bend the second bending portion with respect to the distal end portion of the first bending portion; a position detection portion that is configured to detect that a position of a rigid distal end portion disposed at a distal end of the medical instrument moving in the channel, is a predetermined position of the channel formed in the first bending portion, and send a detection result of the position of the rigid distal end portion of the medical instrument as an input signal; a first bending detection portion that is configured to detect a radius of curvature of an axis of the channel formed in the first bending portion and a direction in which the channel formed in the first bending portion is bent when the input signal is received; a second bending detection portion that is configured to detect a radius of curvature of an axis of the channel formed in the second bending portion and a direction in which the channel formed in the second bending portion is bent when the input signal is received; and a control portion that is configured to control generating a second drive signal driving the second drive portion based on a first drive signal driving the first drive portion, and control sending the second drive signal to the second drive portion while sending the first drive signal to the first drive portion, wherein the control portion generates the first drive signal in a case where the radius of curvature of the axis of the channel formed in the first bending portion is smaller than a predetermined value when the control portion receives the input signal, and the first drive portion releases the holding of the first operation wire based on the first drive signal sent from the control portion, and wherein the second drive signal is generated based on results of the calculation of the radii of curvature by the first bending detection portion and the second bending detection portion, and the second drive portion bends the second bending portion based on the second drive signal sent from the control portion to cause the observation portion to face a treatment target.

According to a second aspect of the invention, in the endoscope device according to the first aspect, the second drive portion may either keep a bending state of the second bending portion, or change the bending state of the second bending portion into a first direction with respect to an axis of the flexible tube portion such that the radius of curvature of the axis of the channel formed in the second bending portion becomes smaller, based on the second drive signal sent from the control portion, when the first bending detection portion detects that the direction in which the channel formed in the first bending portion is bent is the first direction from the axis of the flexible tube portion and the second bending detection portion detects that the direction in which the channel formed in the second bending portion is bent is the first direction from the axis of the flexible tube portion.

According to a third aspect of the invention, in the endoscope device according to the second aspect, the second drive portion may operate to advance and retract a second operation wire which is connected to the second bending portion such that the second bending portion is bent with respect to the distal end portion of the first bending portion, and the first drive portion may change the bending state of the first bending portion into the first direction with respect to the axis of the flexible tube portion, based on the first drive signal sent from the control portion, such that the radius of curvature of the axis of the channel formed in the first bending portion becomes smaller, and the second drive portion may release the holding of the second operation wire based on the second drive signal sent from the control portion, when the position detection portion detects that a position of the rigid distal end portion of the medical instrument is a predetermined position in the channel formed in the first bending portion.

According to a fourth aspect of the invention, in the endoscope device according to the first aspect, the first drive portion may change the bending state of the first bending portion based on the first drive signal sent from the control portion such that the radius of curvature of the axis of the channel formed in the first bending portion becomes larger, and the second drive portion may change the bending state of the second bending portion based on the second drive signal sent from the control portion such that the radius of curvature of the axis of the channel formed in the second bending portion becomes larger, when the second bending detection portion detects that the direction in which the channel formed in the second bending portion is bent, is a first direction with respect to an axis of the flexible tube portion, and the first bending detection portion detects that the direction in which the channel formed in the first bending portion is bent, is a second direction with respect to the axis of the flexible tube portion.

According to a fifth aspect of the invention, in the endoscope device according to the fourth aspect, the first drive portion may change the bending state of the first bending portion based on the first drive signal sent from the control portion, and the second drive portion may change the bending state of the second bending portion based on the second drive signal sent from the control portion, when the position detection portion detects that the position of the rigid distal end portion of the medical instrument is a predetermined position in the channel formed in the first bending portion.

DETAILED DESCRIPTION OF THE INVENTION

First Embodiment

An endoscope device according to a first embodiment of the invention will be described below with reference to FIGS. 1 to 15.

Figure 1:
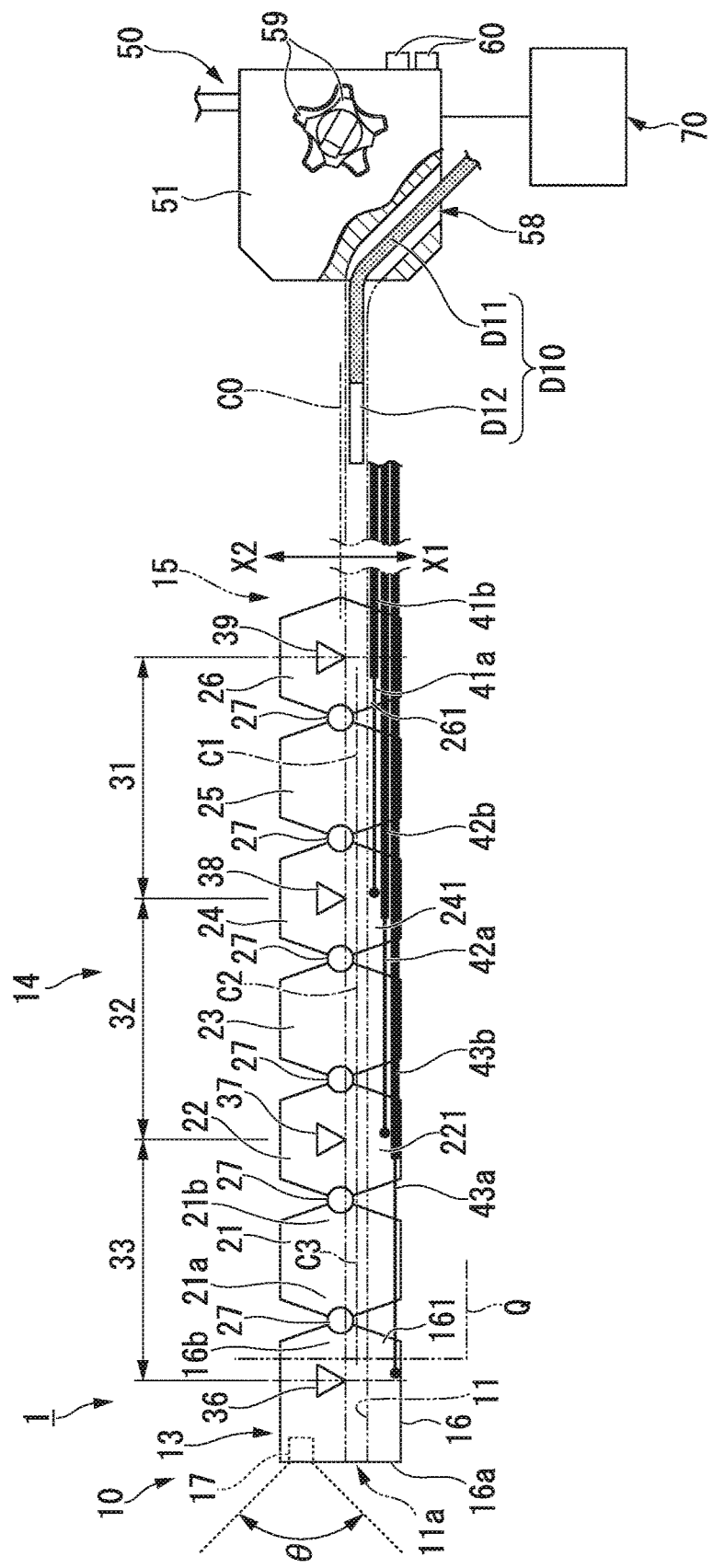
FIG. 1 is a view showing an endoscope device according to a first embodiment of the invention.
Figure 2:
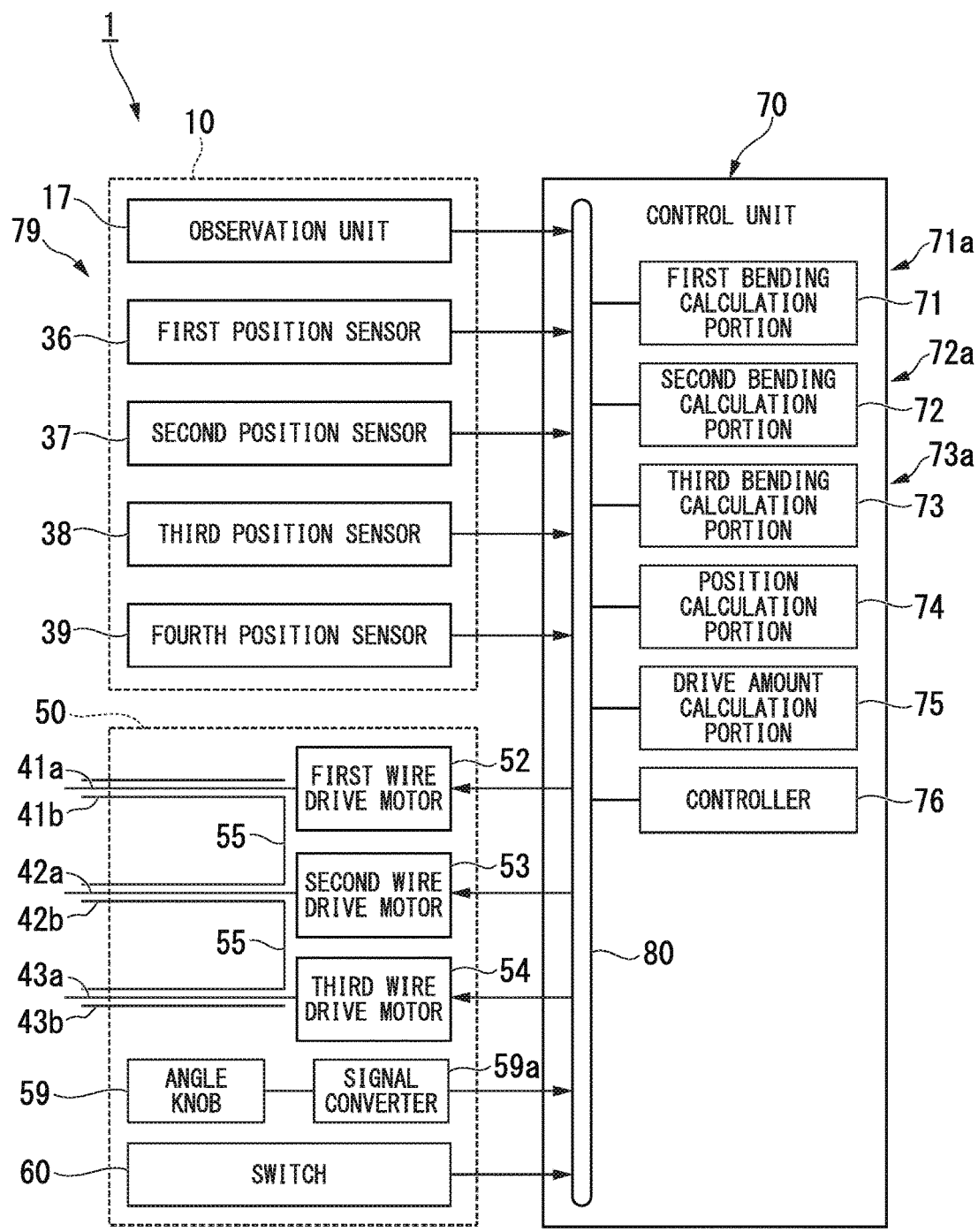
FIG. 2 is a block diagram of the endoscope device according to the first embodiment of the invention.

As shown in FIGS. 1 and 2, an endoscope device 1 according to this embodiment includes an insertion portion 10, an operation portion 50, and a control unit 70. The endoscope device 1 is a so-called direct-view endoscope device that can observe the front of the insertion portion 10. The insertion portion 10 is made of a flexible material, is formed in a columnar shape, and includes a channel 11. The operation portion 50 is provided at a proximal end portion of the insertion portion 10. The control unit 70 is connected to the operation portion 50.

In the following description, a side, which is close to the insertion portion 10 from the operation portion 50 to be described below, will be referred to as a distal end side and a side, which is close to the operation portion 50 from the insertion portion 10, will be referred to as a proximal end side.

In all the following drawings, elements will be schematically shown and only elements important in the description of this embodiment will be shown for convenience of description.

Further, ratios of the thickness or dimensions of each component are adjusted for easy understanding of the drawings.

The insertion portion 10 includes a rigid distal end portion 13, a multi-stage bending portion 14, and a flexible tube portion 15. The rigid distal end portion 13 is provided at a distal end portion of the insertion portion 10. The multi-stage bending portion 14 is disposed more proximal than the rigid distal end portion 13. The flexible tube portion 15 is more proximal than the multi-stage bending portion 14 and is disposed at a proximal end portion of the insertion portion 10.

The rigid distal end portion 13 includes a distal end side of a support member 16 that is made of rigid metal, such as stainless steel, and is formed in a cylindrical shape. For example, a distal end portion of an illumination unit, which includes a light guide (not shown), and an observation unit (an observation portion) 17 that includes an imaging element, such as a charge coupled device (CCD), are fixed to a distal end surface 16a of the support member 16, that is, to a portion, which is more distal than a second bending portion 32 to be described below, in a state in which the distal end portion of the illumination unit and the observation unit are exposed to the outside. The observation unit 17 acquires an image within the angle θ of view on the front of the distal end surface 16a of the insertion portion 10; converts data, which represent the acquired image, into signals; and sends the signals to the control unit 70. The observation unit 17 is provided more distal than the multi-stage bending portion 14 of the insertion portion 10.

An opening 11a of a distal end portion of the channel 11 is formed on the distal end surface 16a of the support member 16. The channel 11 is formed along an axis of the insertion portion 10.

A pair of proximal end-side protruding portions 16b, which protrude toward the proximal end side at positions spaced from each other in the radial direction of the support member 16, are provided at a proximal end portion of the support member 16 (only one of each of the pair of proximal end-side protruding portions 16b and a pair of pins 27, and the like is shown in the following drawings).

The multi-stage bending portion 14 is made of metal, such as stainless steel, and is formed in a cylindrical shape. The multi-stage bending portion 14 includes six joint rings 21 to 26 that are disposed side by side toward the proximal end side from the distal end side. Since the joint rings 21 to 26 have the same shape, the joint ring 21 will be described.

A pair of distal end side protruding portions 21a, which protrude toward the distal end side at positions spaced from each other in the radial direction of the joint ring 21, are provided at a distal end portion of the joint ring 21. A pair of proximal end-side protruding portions 21b, which protrude toward the proximal end side at positions spaced from each other in the radial direction of the joint ring 21, are provided at a proximal end portion of the joint ring 21.

A proximal end-side protruding portion 16b of the support member 16 and a distal end side protruding portion 21a of the joint ring 21 are connected to each other by a pin 27. The other proximal end-side protruding portion 16b of the support member 16 and the other distal end side protruding portion 21a of the joint ring 21 are connected to each other by a pin 27.

The joint ring 21 and the joint ring 22 are connected to each other by a pair of pins 27, the joint ring 22 and the joint ring 23 are connected to each other by a pair of pins 27, the joint ring 23 and the joint ring 24 are connected to each other by a pair of pins 27, and the joint ring 25 and the joint ring 26 are connected to each other by a pair of pins 27. The axes of the respective pins 27 are parallel to each other.

The joint ring 25 can oscillate on a virtual plane Q, which is orthogonal to the axis of the pin 27, with respect to the joint ring 26. Likewise, the joint ring 24 can oscillate on the virtual plane Q with respect to the joint ring 25, the joint ring 23 can oscillate on the virtual plane Q with respect to the joint ring 24, the joint ring 22 can oscillate on the virtual plane Q with respect to the joint ring 23, the joint ring 21 can oscillate on the virtual plane Q with respect to the oscillate on the virtual plane Q with respect to the joint ring 22, and the support member 16 can oscillate on the virtual plane Q with respect to the joint ring 21.

A third bending portion 33 includes a proximal end side of the support member 16, distal end sides of the joint rings 21 and 22, pins 27 that connect the support member 16 to the joint ring 21, and pins 27 that connect the joint ring 21 to the joint ring 22. A second bending portion 32 includes a proximal end side of the joint ring 22, distal end sides of the joint rings 23 and 24, pins 27 that connect the joint ring 22 to the joint ring 23, and pins 27 that connect the joint ring 23 to the joint ring 24. A first bending portion 31 includes a proximal end side of the joint ring 24, distal end side of the joint rings 25 and 26, pins 27 that connect the joint ring 24 to the joint ring 25, and pins 27 that connect the joint ring 25 to the joint ring 26.

A proximal end side of the joint ring 26 forms a distal end portion of the flexible tube portion 15.

The multi-stage bending portion 14 includes three bending portions 31 to 33 that are referred to as the first bending portion 31, the second bending portion 32, and the third bending portion 33. The bending portions 31 to 33 are disposed more proximal than the opening 11a of the channel 11.

The first bending portion 31 is provided more distal than the flexible tube portion 15 of the insertion portion 10 and can be bent from the distal end portion of the flexible tube portion 15. The second bending portion 32 is provided more distal than the first bending portion 31 of the insertion portion 10 and can be bent from a distal end portion of the first bending portion 31. Further, the third bending portion 33 is provided more distal than the second bending portion 32 of the insertion portion 10 and can be bent from a distal end portion of the second bending portion 32.

In the present embodiment, a distal end of the first bending portion 31 and a proximal end of the second bending portion 32 are directly connected to each other without other members interposed therebetween. A distal end of the second bending portion 32 and a proximal end of the third bending portion 33 are directly connected to each other without other members interposed therebetween.

The lengths of the bending portions 31 to 33 in the direction of the axis of the insertion portion 10 are equal to each other.

A first position sensor 36 is provided on the channel 11 at a position on a boundary between the rigid distal end portion 13 and the third bending portion 33. Likewise, a second position sensor 37 is provided on the channel 11 at a position on a boundary between the third bending portion 33 and the second bending portion 32. A third position sensor 38 is provided on the channel 11 at a position on a boundary between the second bending portion 32 and the first bending portion 31. A fourth position sensor 39 is provided on the channel 11 at a position on a boundary between the first bending portion 31 and the flexible tube portion 15.

Since these first to fourth position sensors 36 to 39 have the same structure, the third and fourth position sensors 38 and 39 will be described as examples.

Figure 3:
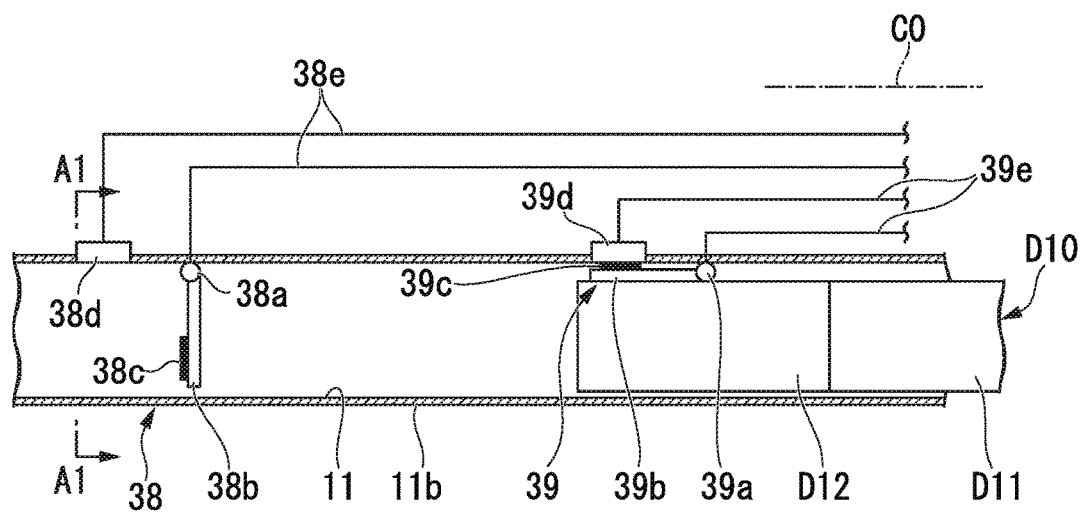
FIG. 3 is a side sectional view showing position sensors of the endoscope device according to the first embodiment of the invention.

FIG. 3 schematically shows a treatment tool (a medical instrument) D10 where a rigid portion (a rigid distal end portion) D12 is provided at a distal end portion of a flexible treatment tool-insertion portion D11. The treatment tool D10 is, for example, a pair of biopsy forceps and the rigid portion D12 is, for example, a pair of forceps pieces or the like. The length of the rigid portion D12 is sufficiently shorter than the length of the channel 11, which is formed in the first bending portion 31, in the direction of the axis of the insertion portion 10.

Whether or not the rigid portion D12 of the treatment tool D10 can be inserted into the channel 11 formed in the first bending portion 31 is determined according to the outer diameter of the rigid portion D12 and the radius of curvature of an axis (a center line) C1 of the channel 11 formed in the first bending portion 31 shown in FIG. 1. That is, the rigid portion D12 may be caught by the inner peripheral surface of the channel 11 formed in the first bending portion 31 in a case in which the outer diameter of the rigid portion D12 is close to the inner diameter of the channel 11 formed in the first bending portion 31. Accordingly, there is a case that it is difficult for the rigid portion D12 to be inserted into the channel 11.

In a state in which the first bending portion 31 is bent, the channel 11 formed in the first bending portion 31 is also bent with a radius of curvature substantially equal to the radius of curvature of the axis of the first bending portion 31. Accordingly, as the radius of curvature of the axis of the first bending portion 31 becomes smaller, the radius of curvature of the axis C1 of the channel 11 formed in the first bending portion 31 also becomes smaller. Accordingly, there is a case in which it is difficult for the rigid portion D12 to be inserted into the channel 11 deformed with a small radius of curvature.

Likewise, whether or not the rigid portion D12 can be inserted into the channel 11 formed in the second bending portion 32 is determined according to the radius of curvature of an axis (a center line) C2 of the channel 11 formed in the second bending portion 32.

Whether or not the rigid portion D12 can be inserted into the channel 11 formed in the third bending portion 33 is determined according to the radius of curvature of an axis (a center line) C3 of the channel 11 formed in the third bending portion 33.

Figure 4:
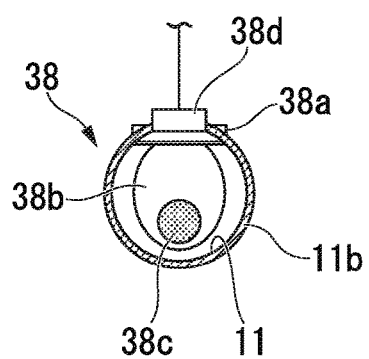
FIG. 4 is a cross-sectional view taken along line A1-A1 of FIG. 3.

As shown in FIGS. 3 and 4, the third position sensor 38 includes a rotating shaft member 38a, a shutter 38b, a contact point (a contact surface) 38c, and a contact point (a contacted surface) 38d. The rotating shaft member 38a is mounted on a tube 11b in which the channel 11 is formed. A first end portion of the shutter 38b is supported so as to be rotatable about the rotating shaft member 38a. The contact point (a contact surface) 38c is mounted on the surface, which faces the distal end side, of a second end portion of the shutter 38b. The contact point (a contacted surface) 38d is mounted on the tube 11b so as to be exposed to the inside of the channel.

In a state in which the shutter 38b is not in contact with the treatment tool D10, the shutter 38b is biased by a spring member (not shown) or the like. Accordingly, the shutter 38b is disposed so as to close the channel 11. The contact point 38d is disposed at a position where the contact point 38d can come into contact with the contact point 38c when the shutter 38b is rotated about the rotating shaft member 38a.

End portions of wires 38e are connected to the contact points 38c and 38d.

The action of the third position sensor 38 will be described using the fourth position sensor 39.

As in the case of the third position sensor 38, the fourth position sensor 39 includes a rotating shaft member 39a, a shutter 39b, a contact point 39c, a contact point 39d, and a pair of wires 39e.

The pair of wires 39e are insulated from each other in an initial state in which the shutter 39b is not in contact with the treatment tool D10.

An operator inserts the treatment tool D10 into the channel 11 from the proximal end side of the channel 11 and moves the treatment tool D10 to the distal end side (the operator pushes the treatment tool D10 into the channel 11) from the channel 11. At this time, the rigid portion D12 pushes the shutter 39b toward the distal end side against the elastic force of the spring member, so that the shutter 39b is rotated about the rotating shaft member 39a. When the distal end of the rigid portion D12 is moved to the position on the boundary between the first bending portion 31 and the flexible tube portion 15 in the direction of an axis (a center line) C0 of the flexible tube portion 15, a state in which the contact point 39c comes into contact with the contact point 39d and the pair of wires 39e are electrically connected to each other is kept. Accordingly, the position of the rigid portion D12 of the treatment tool D10 in the channel 11, when the contact point 39c comes into contact with the contact point 39d, is detected.

Even though the treatment tool D10 is further advanced in the channel 11, a state in which the contact point 39c comes into contact with the contact point 39d and the pair of wires 39e are electrically connected to each other is kept.

When viewed in the direction of the axis C0 of the flexible tube portion 15, two portions of the joint ring between the pins 27 in a circumferential direction are referred to as a first side portion and a second side portion. The first side portion and the second side portion are positioned on both sides of the axis C0 (a first direction X1 and a second direction X2 indicated in FIG. 1 by arrows X1 and X2). As shown in FIG. 1, a distal end portion of a first operation-main wire (a first operation wire) 41a is connected to a first side portion 241 (positioned in the first direction X1 from the axis C0 of the flexible tube portion 15), which is at the proximal end side (the distal end portion of the first bending portion 31), of the joint ring 24 by welding or the like. The first operation-main wire 41a is inserted into a coil sheath 41b. A distal end portion of the coil sheath 41b is connected to a first side portion 261 (positioned in the first direction X1 from the axis C0) of the joint ring 26 by welding or the like. The distal end portion of the first operation-main wire 41a is fixed to the inner peripheral surface of the joint ring 24, and the distal end portion of the coil sheath 41b is fixed to the inner peripheral surface of the joint ring 26.

When the first operation-main wire 41a is moved (pulled back) to the proximal end side from the coil sheath 41b, the first bending portion 31 is bent in (toward) the first direction X1 from the axis C0. When the first operation-main wire 41a is moved (pushed) to the distal end side from the coil sheath 41b, the first bending portion 31 is bent in (toward) the second direction X2 from the axis C0.

A direction in which the first bending portion 31 is bent means a direction in which the distal end portion of the first bending portion 31 is deflected from the central axis of the proximal end of the first bending portion 31. The same applies to the second bending portion 32, the third bending portion 33, the channel 11 formed in the first bending portion 31, the channel 11 formed in the second bending portion 32, and the channel 11 formed in the third bending portion 33.

The insertion portion 10 includes a second operation-main wire (a second operation wire) 42a, a coil sheath 42b, a third operation-main wire 43a, and a coil sheath 43b. The second operation-main wire 42a and the third operation-main wire 43a have the same structure as the structure of the first operation-main wire 41a. The coil sheath 42b and the coil sheath 43b have the same structure as the structure of the coil sheath 41b.

Specifically, a distal end portion of the second operation-main wire 42a is connected to a first side portion 221, which is at the proximal end side (the distal end portion of the second bending portion 32), of the joint ring 22. The second operation-main wire 42a is inserted into the coil sheath 42b. A distal end portion of the coil sheath 42b is connected to the first side portion 241 of the joint ring 24. When the second operation-main wire 42a is pulled back from the coil sheath 42b, the second bending portion 32 is bent in the first direction X1 from the axis C0.

A distal end portion of the third operation-main wire 43a is connected to a first side portion 161, which is at the proximal end side, of the support member 16. The third operation-main wire 43a is inserted into the coil sheath 43b. A distal end portion of the coil sheath 43b is connected to the first side portion 221 of the joint ring 22. The actions of the third operation-main wire 43a, the coil sheath 43b, and the third bending portion 33 are the same as the action of the first bending portion 31.

When the first operation-main wire 41a is advanced or retracted in this way, the first bending portion 31 can be bent from the distal end portion of the flexible tube portion 15. Likewise, when the second operation-main wire 42a is advanced or retracted, the second bending portion 32 can be bent from the distal end portion of the first bending portion 31. When the third operation-main wire 43a is advanced or retracted, the third bending portion 33 can be bent from the distal end portion of the second bending portion 32.

Since the support member 16 is made of a rigid material, a distance between the distal end of the third bending portion 33 and the observation unit 17 and the direction of the observation unit 17 relative to the distal end of the third bending portion 33 are not changed even though the bending portions 31 to 33 are bent.

The bending portions 31 to 33 can be freely bent on the virtual plane Q from the distal end surface of the flexible tube portion 15 (the proximal end portion of the joint ring 26).

As shown in FIGS. 1 and 2, the operation portion 50 includes an operation portion main body 51, and a first wire drive motor (a first drive portion) 52, a second wire drive motor (a second drive portion) 53, a third wire drive motor 54, and support members 55 that are provided in the operation portion main body 51.

The wire drive motors 52 to 54 and the support members 55 are fixed to the operation portion main body 51.

A proximal end portion of the first operation-main wire 41a is connected to a rotating shaft (not shown) of the first wire drive motor 52. A proximal end portion of the coil sheath 41b into which the first operation-main wire 41a is inserted is fixed to the support member 55.

Likewise, a proximal end portion of the second operation-main wire 42a is connected to a rotating shaft (not shown) of the second wire drive motor 53. A proximal end portion of the coil sheath 42b into which the second operation-main wire 42a is inserted is fixed to the support member 55. A proximal end portion of the third operation-main wire 43a is connected to a rotating shaft (not shown) of the third wire drive motor 54. A proximal end portion of the coil sheath 43b into which the third operation-main wire 43a is inserted is fixed to the support member 55.

When power is supplied to the first wire drive motor 52, the rotating shaft of the first wire drive motor 52 is rotated in a first direction. Accordingly, the first operation-main wire 41a is pulled back to the proximal end side from the coil sheath 41b, so that the first bending portion 31 is bent in the first direction X1 from the axis C0. On the other hand, when the rotating shaft of the first wire drive motor 52 is rotated in a direction opposite to the first direction, the first operation-main wire 41a is pushed. Accordingly, the first bending portion 31 is bent in the second direction X2 from the axis C0.

When the supply of power to the first wire drive motor 52 is stopped, the rotating shaft of the first wire drive motor 52 can be freely rotated. That is, it is possible to release a state in which the rotational drive of the rotating shaft of the first wire drive motor 52 in the first direction or a direction opposite to the first direction is controlled. In this case, the first bending portion 31 can be easily bent in the first direction X1 or the second direction X2 by an external force (the fixing of the bent shape of the first bending portion 31 is released).

Likewise, when power is supplied to the second wire drive motor 53, the rotating shaft of the second wire drive motor 53 is rotationally driven. Accordingly, the second bending portion 32 is bent in the first direction X1 or the second direction X2. When power is supplied to the third wire drive motor 54, the rotating shaft of the third wire drive motor 54 is rotationally driven. Accordingly, the third bending portion 33 is bent in the first direction X1 or the second direction X2.

When the supply of power to the second wire drive motor 53 is stopped, the second bending portion 32 can be easily bent by an external force. When the supply of power to the third wire drive motor 54 is stopped, the third bending portion 33 can be easily bent by an external force.

The first operation-main wire 41a, the second operation-main wire 42a, and the third operation-main wire 43a can be operated in this way by the wire drive motors 52 to 54 of the operation portion 50. The first bending portion 31, the second bending portion 32, and the third bending portion 33 can be bent independently of each other by the operation portion 50.

A potentiometer (not shown) is built in each of the wire drive motors 52 to 54. The rotation angle of each of the rotating shafts of the wire drive motors 52 to 54 from a reference position is detected by the potentiometer. The potentiometers convert detection results into signals and send the signals to the control unit 70. The potentiometers may be provided outside the wire drive motors 52 to 54.

In the present embodiment, the bending portions 31 to 33 are bent on the virtual plane Q in the first direction X1 and the second direction X2. The bending portions 31 to 33 may be adapted to be bent in four directions corresponding to equal angles around the axis C0.

As shown in FIG. 1, a forceps port 58 is provided on the distal end side of the operation portion main body 51. A proximal end portion of the channel 11 communicates with the forceps port 58. That is, the proximal end portion of the channel 11 is opened at a position more proximal than the multi-stage bending portion 14.

An angle knob 59, which is used to operate the above-mentioned wire drive motors 52 to 54 through a control portion 76 to be described below, is provided at the proximal end side of the operation portion main body 51.

A signal converter 59a, which converts the rotation angle of the angle knob 59 into a signal, is connected to the angle knob 59 (see FIG. 2). An operator can bend the multi-stage bending portion 14 in a desired direction by operating the angle knob 59 when the control mode is a manual operation mode as described below.

The operation portion main body 51 is provided with switches 60 that are used to input the type of the treatment tool D10 to be inserted into the channel 11.

The control unit 70 includes a first bending calculation portion 71, a second bending calculation portion 72, a third bending calculation portion 73, a position calculation portion 74, a drive amount calculation portion 75, and a control portion 76. The first bending calculation portion 71 performs calculation processing based on a signal sent from the potentiometer of the first wire drive motor 52. The second bending calculation portion 72 performs calculation processing based on a signal sent from the potentiometer of the second wire drive motor 53. The third bending calculation portion 73 performs calculation processing based on a signal sent from the potentiometer of the third wire drive motor 54. The position calculation portion 74 detects the position of the rigid portion D12 of the treatment tool D10 from the detection results of the first to fourth position sensors 36 to 39. The drive amount calculation portion 75 calculates the drive amounts of the wire drive motors 52 to 54 based on the signals sent from the angle knob 59 or a position detection portion 79 to be described below. The control portion 76 controls the operation portion 50.

The first position sensor 36, the second position sensor 37, the third position sensor 38, the fourth position sensor 39, and the position calculation portion 74 form the position detection portion 79.

The first bending calculation portion 71 and the potentiometer, which is built in the first wire drive motor 52, form a first bending detection portion 71a. The second bending calculation portion 72 and the potentiometer, which is built in the second wire drive motor 53, form a second bending detection portion 72a. The third bending calculation portion 73 and the potentiometer, which is built in the third wire drive motor 54, form a third bending detection portion 73a.

These bending calculation portions 71 to 73, the position calculation portion 74, the drive amount calculation portion 75, and the control portion 76 are connected to a bus 80.

The observation unit 17, the position sensors 36 to 39, the wire drive motors 52 to 54, the signal converter 59a, and the switches 60 are connected to the bus 80.

Although not shown, each of the bending calculation portions 71 to 73, the position calculation portion 74, the drive amount calculation portion 75, and the control portion 76 includes an arithmetic element, a memory, a control program, and the like.

When the rotating shaft of the first wire drive motor 52 is rotated from the reference position in the first direction, the first operation-main wire 41a is pulled back to the proximal end side from a neutral position where the first bending portion 31 has a straight shape. Accordingly, the first bending portion 31 is bent in the first direction X1 from the axis C0. Therefore, the radius of curvature of the axis C1 of the channel 11, which is formed in the first bending portion 31, becomes a predetermined radius of curvature. When the rotating shaft of the first wire drive motor 52 is rotated from the reference position in a direction opposite to the first direction, the first operation-main wire 41a is pushed to the distal end side from the neutral position where the first bending portion 31 has a straight shape. Accordingly, the first bending portion 31 is bent in the second direction X2 from the axis C0. Therefore, the radius of curvature of the axis C1 of the channel 11, which is formed in the first bending portion 31, has a predetermined value.

As described above, there is a certain correspondence relationship among the length of the first operation-main wire 41a that is pulled back or pushed from the neutral position of the first bending portion 31, the radius of curvature of the axis C1 of the channel 11 formed in the first bending portion 31, and a direction in which the channel 11 formed in the first bending portion 31 is bent.

The same applies to the second operation-main wire 42a and the third operation-main wire 43a. That is, there is a certain correspondence relationship among the length of the second operation-main wire 42a that is pulled back or pushed from the neutral position of the second bending portion 32, the radius of curvature of the axis C2 of the channel 11 formed in the second bending portion 32, and a direction in which the channel 11 formed in the second bending portion 32 is bent. There is a certain correspondence relationship among the length of the third operation-main wire 43a that is pulled back or pushed from the neutral position of the third bending portion 33, the radius of curvature of the axis C3 of the channel 11 formed in the third bending portion 33, and a direction in which the channel 11 formed in the third bending portion 33 is bent.

A table representing a correspondence relationship between the rotation angle of the rotating shaft of the first wire drive motor 52 from the reference position and the radius of curvature of the axis C1 of the channel 11 formed in the first bending portion 31, which is obtained when the first bending portion 31 is bent, is stored in the memory of the first bending calculation portion 71.

The arithmetic element of the first bending calculation portion 71 calculates the radius of curvature of the axis C1 of the channel 11, which is formed in the first bending portion 31, from a signal which represents the rotation angle of the rotating shaft of the first wire drive motor 52 and is sent from the potentiometer, based on the table stored in the memory.

A direction in which the first bending portion 31 is bent is calculated from the direction of the rotation of the rotating shaft of the first wire drive motor 52 from the reference position.

In this way, the first bending detection portion 71*a* calculates the radius of curvature of the axis C1 of the channel 11, which is formed in the first bending portion 31, and a direction in which the first bending portion 31 is bent.

Likewise, the second bending detection portion 72*a* calculates the radius of curvature of the axis C2 of the channel 11, which is formed in the second bending portion 32, and a direction in which the second bending portion 32 is bent. The third bending detection portion 73*a* calculates the radius of curvature of the axis C3 of the channel 11, which is formed in the third bending portion 33, and a direction in which the third bending portion 33 is bent.

The position calculation portion 74 calculates the position of the rigid portion D12 in the channel 11 from the detection results of the respective first to fourth position sensors 36 to 39. The position detection portion 79 calculates the position of the rigid portion D12 of the treatment tool D10, which moves in the channel 11, and sends the result of the calculation of the position of the rigid portion D12 of the treatment tool D10 to the control portion 76 as an input signal.

The control portion 76 has a manual operation mode and an automatic operation mode as a control mode. Immediately after the endoscope device 1 is started up, the control mode becomes the manual operation mode. The manual operation mode is a control mode in which the bending portion can be operated by the input of an operation from the operation portion in addition to the control performed by the control portion 76. The automatic operation mode is a control mode in which the input of an operation except for the control performed by the control portion 76 is not received.

In the manual operation mode, the bending portions 31 to 33 operate as described below when an operator operates the angle knob 59, for example, to instruct the multi-stage bending portion 14 to be bent in the first direction X1 from the axis C0 by a central angle $3\alpha$.

The drive amount calculation portion 75 calculates an angle $\alpha$, which is obtained by dividing the central angle $3\alpha$ of the entire multi-stage bending portion 14 by 3 (which is the number of the bending portions 31 to 33), as a bending angle of each of the bending portions 31 to 33. The result of the calculation of the bending angle of each of the bending portions 31 to 33 is sent to the control portion 76. The control portion 76 bends the respective bending portions 31 to 33 equally by the angle $\alpha$. In this example, the bending portions 31 to 33 are not directly connected to the angle knob 59 by the operation-main wires.

In this case, the multi-stage bending portion 14 can be operated as if the bending portions 31 to 33 are operated by only one operation wire.

When the position of the distal end of the rigid portion D12 is detected by the position calculation portion 74, the control mode of the control portion 76 is automatically switched to the automatic operation mode from the manual operation mode.

In the automatic operation mode, the control portion 76 controls the operation portion 50 based on the detection results of the bending detection portions 71*a* to 73*a* and the position calculation portion 74. When the control mode is the automatic operation mode, a clutch mechanism (not shown) is provided so as not to allow the bending portions 31 to 33 to be bent even though an operator operates the angle knob 59, or the angle knob 59 is locked so that an operator cannot operate the angle knob 59.

In the automatic operation mode, the control portion 76 automatically controls the bending portions 31 to 33 based on the radii of curvature of the axes C1 to C3 of the channel 11, which is formed in the bending portions 31 to 33, and directions in which the bending portions 31 to 33 are bent. The details of the automatic operation mode will be described below.

The endoscope device 1 and the treatment tool D10 form an endoscope system.

For example, a table representing a correspondence relationship between the type of the treatment tool D10 and predetermined values, which represent the radii of curvature of the axes C1 to C3 of the channel 11 formed in the bending portions 31 to 33, is stored in the memory of the control portion 76. That is, a table in which values of the radii of curvature of the axes C1 to C3 of the channel 11, which are required to allow the treatment tool D10 to be inserted into the channel 11, are associated with each of types of the treatment tool D10 is stored in the memory of the control portion 76.

Figure 5:
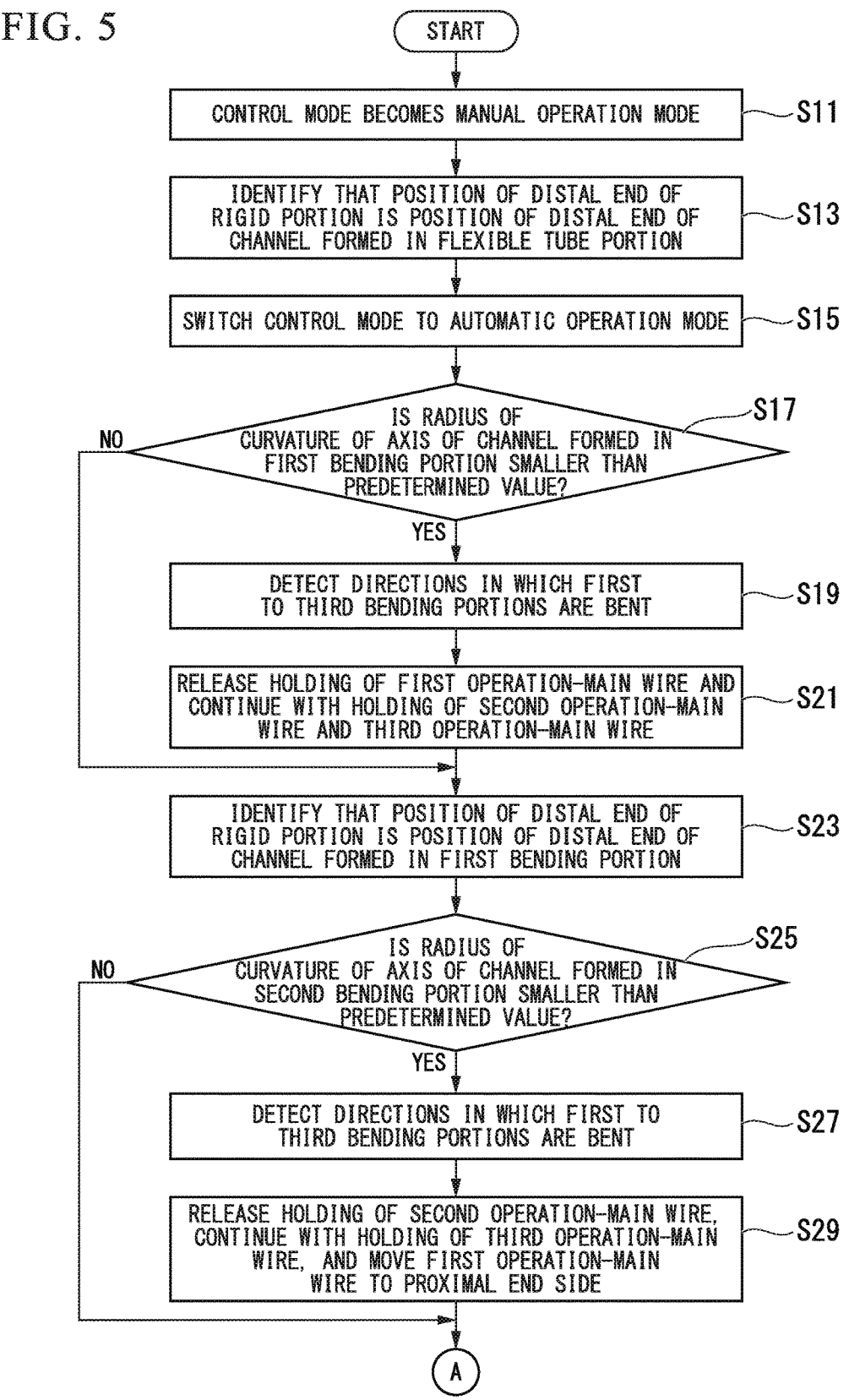
FIG. 5 is a flowchart showing the action of the endoscope device according to the first embodiment of the invention.
Figure 6:
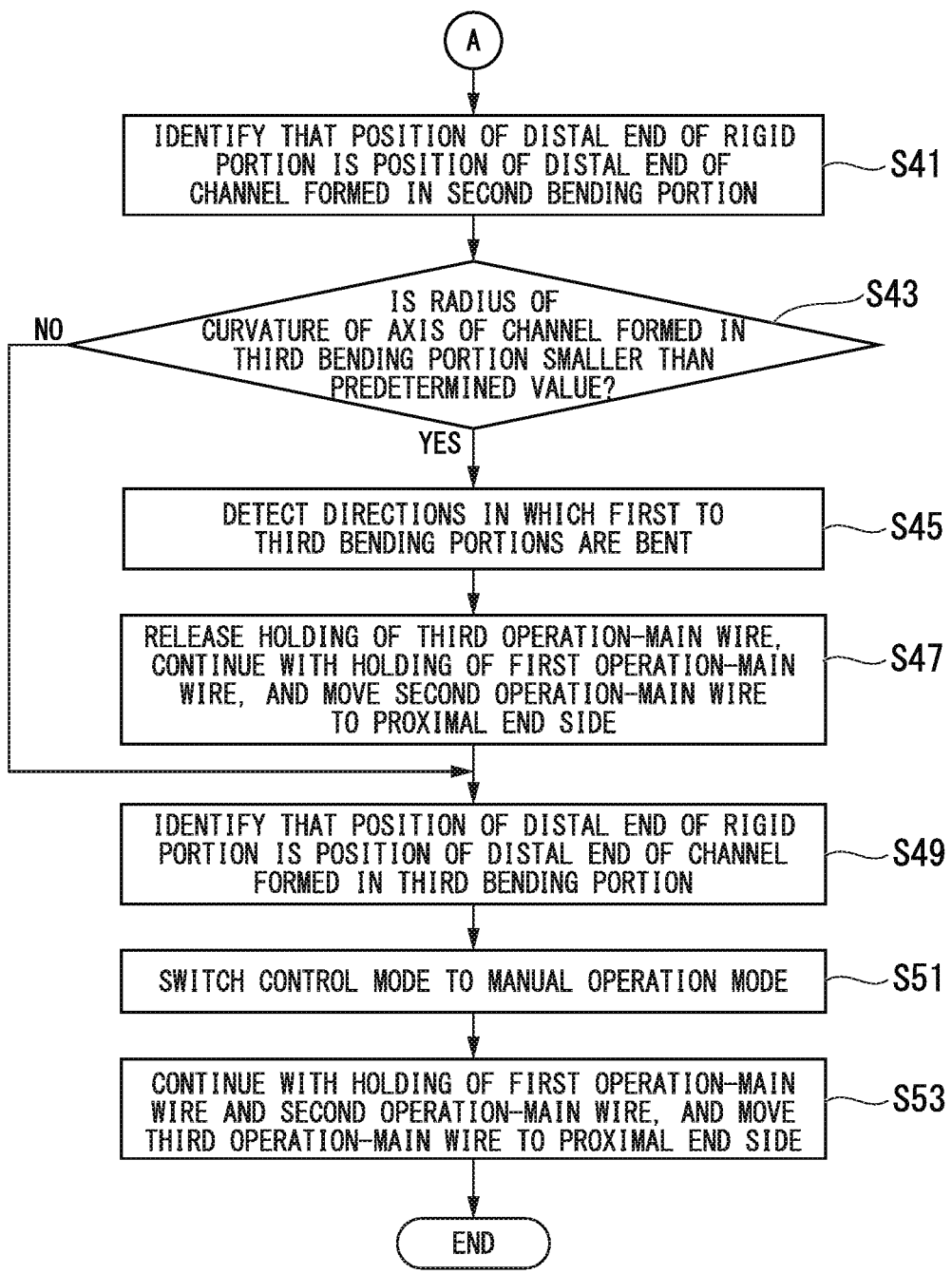
FIG. 6 is a flowchart showing the action of the endoscope device according to the first embodiment of the invention.

Next, the action of the endoscope device 1 having the above-mentioned structure will be described. For example, an operation for performing a treatment for a mucous membrane present in a body cavity by using the endoscope device 1 will be described below. FIGS. 5 and 6 are flowcharts showing the action of the endoscope device 1.

First, an operator, such as a practitioner, starts up the endoscope device 1 by operating switches (not shown) to supply power to the observation unit 17, the control unit 70, a light source, and the like from a power source (not shown).

At this time, the control mode of the control portion 76 becomes the manual operation mode (Step S11).

Illumination light, which is emitted from the light source, is supplied to the light guide, and illumination light, which is guided by the light guide, is emitted to the front of the insertion portion 10.

The observation unit 17 acquires an image within the angle $\theta$ of view, converts the image into signals, and sends the signals to a monitor through the operation portion 50. The sent signals are converted into an image, and the image is displayed on the monitor.

The operator introduces the insertion portion 10 into the body cavity from a patient's mouth or the like while observing the image, which is acquired by the observation unit 17 of the endoscope device 1, through the monitor.

The operator operates the angle knob 59 as necessary, and introduces the insertion portion 10 into the body cavity. At this time, the respective bending portions 31 to 33 are bent equally in the first direction X1 or the second direction X2 from the axis C0.

Figure 7:
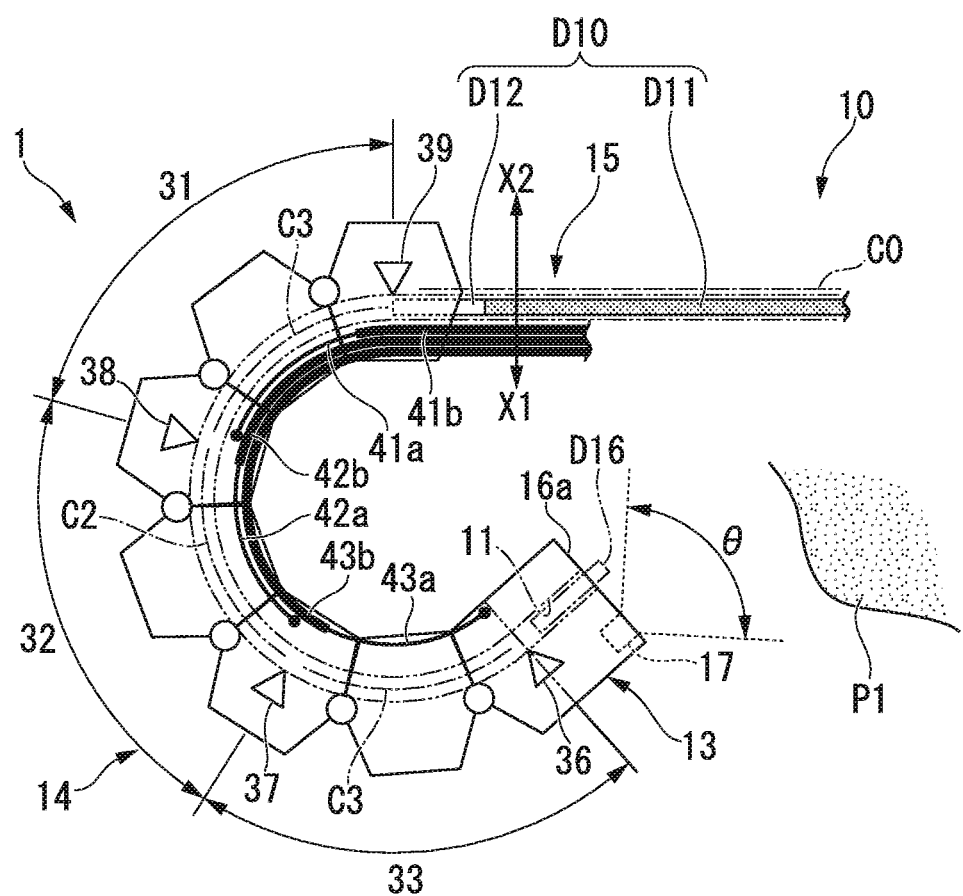
FIG. 7 is a view showing the action of the endoscope device according to the first embodiment of the invention.

As shown in FIG. 7, the operator makes the distal end surface 16*a* of the insertion portion 10 face a treatment target P1 so that the treatment target P1 is within the angle $\theta$ of view. At this time, the treatment target P1 is within the field of view of the observation unit 17.

All the bending portions 31 to 33 are bent in the first direction X1 from the axis C0. The radii of curvature of the axes C1 to C3 of the channel 11 formed in the bending portions 31 to 33 are smaller than the above-mentioned predetermined values. That is, the bending states of the bending portions 31 to 33 are changed (the bending portions 31 to 33 are extremely bent) so that the radii of curvature of the axes C1 to C3 of the channel 11 formed in the bending portions 31 to 33 become smaller than the predetermined values. The wire drive motors 52 to 54 hold the operation-main wires 41a to 43a that have been pulled back.

A state in which all the bending portions 31 to 33 are bent to the same side from the axis C0 in this way will be referred to as "the bending portions 31 to 33 are bent in a J shape" hereinafter.

The position of the insertion portion 10 relative to the treatment target P1 is held.

The operator inputs the type of the treatment tool D10, which is to be inserted into the channel 11, by the switches 60 of the operation portion 50. The arithmetic element of the control portion 76 obtains predetermined values, which represent the radii of curvature of the axes C1 to C3 of the channel 11 formed in the bending portions 31 to 33 and correspond to the type of the treatment tool D10, from the table stored in the memory.

The operator grasps the operation portion main body 51 with one hand, grasps the proximal end portion of the treatment tool D10 with the other hand, and inserts the rigid portion D12 of the treatment tool D10 into the channel 11 through the forceps port 58.

In Step S13 shown in FIG. 5, the control portion 76 identifies position information about whether or not the position of the distal end of the rigid portion D12 is positioned at the distal end (a predetermined position) of the channel 11 formed in the flexible tube portion 15, based on an input signal sent from the position detection portion 79.

It is preferable that the fourth position sensor 39 is disposed at the distal end portion of the channel 11 formed in the flexible tube portion 15, but the fourth position sensor 39 may be disposed at an arbitrary position on the channel 11 formed in the flexible tube portion 15. Accordingly, the position of the fourth position sensor 39 is not limited to the position of the distal end portion of the channel 11 formed in the flexible tube portion 15.

If the control portion 76 identifies that the rigid portion D12 of the treatment tool D10 is positioned at the distal end portion of the channel 11 formed in the flexible tube portion 15, the control portion 76 proceeds to Step S15 from Step S13.

In Step S15, the control portion 76 switches the control mode to the automatic operation mode from the manual operation mode and proceeds to Step S17.

In Step S17, the control portion 76 determines whether or not the radius of curvature of the axis C1 of the channel 11 formed in the first bending portion 31 is smaller than a predetermined value. When the first bending detection portion 71a receives an input signal sent from the position detection portion 79, the first bending detection portion 71a calculates the radius of curvature of the axis C1 of the channel 11 formed in the first bending portion 31 and a direction in which the first bending portion 31 is bent. In this case, since the radius of curvature of the axis C1 of the channel 11 formed in the first bending portion 31, which is calculated by the first bending detection portion 71a, is smaller than a predetermined value, the control portion 76 determines "YES" in Step S17 and proceeds to Step S19.

In Step S19, the bending detection portions 71a to 73a detect that all directions in which the bending portions 31 to 33 are bent are the first direction X1 from the axis C0 of the flexible tube portion 15, and send these detection results to the control portion 76. The control portion 76 proceeds to Step S21.

Figure 8:
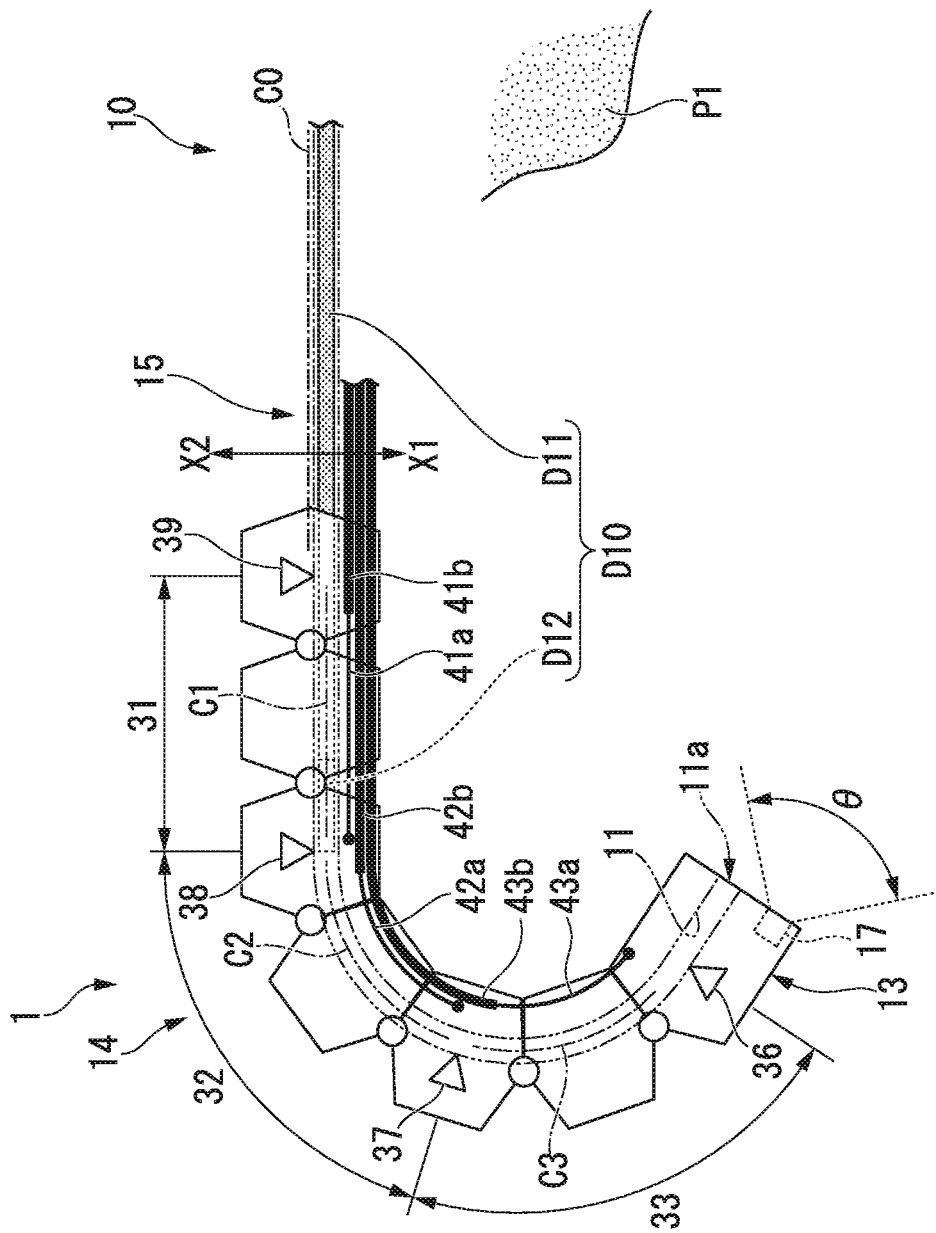
FIG. 8 is a view showing the action of the endoscope device according to the first embodiment of the invention.

In Step S21, as shown in FIG. 8, the control portion 76 releases the holding of the first operation-main wire 41a by the first wire drive motor 52 through the operation portion 50 and continues with the holding of the second operation-main wire 42a and the third operation-main wire 43a.

At this time, the control portion 76 generates a first drive signal that stops the supply of power to the first wire drive motor 52. The control portion 76 generates a second drive signal, which drives the second wire drive motor 53, based on the result of the calculation of the radius of curvature of the axis C1 of the channel 11 formed in the first bending portion 31, which is performed by the first bending detection portion 71a, and the first drive signal. Then, the control portion 76 generates a third drive signal that drives the third wire drive motor 54. The control portion 76 sends the first drive signal to the first wire drive motor 52, sends the second drive signal to the second wire drive motor 53, and sends the third drive signal to the third wire drive motor 54.

Since the holding of the first operation-main wire 41a, which is performed by the first wire drive motor 52, is released, the first bending portion 31 is easily bent in the first direction X1 or the second direction X2 from the axis C0 when the operator inserts the treatment tool D10. Accordingly, the first bending portion 31 becomes substantially straight along the shape of the rigid portion D12. The bending state of the bending portion 32 is kept (the second bending portion 32 continues to be extremely bent) so that the radius of curvature of the axis C2 of the channel 11 formed in the second bending portion 32 is smaller than a predetermined value, and the bending state of the bending portion 33 is being kept (the third bending portion 33 continues to be extremely bent) so that the radius of curvature of the axis C3 of the channel 11 formed in the third bending portion 33 is smaller than a predetermined value.

The second wire drive motor 53 keeps the bending state of the second bending portion 32 based on the second drive signal sent from the control portion 76. The third wire drive motor 54 keeps the bending state of the third bending portion 33 based on the third drive signal sent from the control portion 76.

If the control portion 76 determines in Step S17 that the radius of curvature of the axis C1 of the channel 11 formed in the first bending portion 31 is equal to or larger than a predetermined value (NO), the control portion 76 proceeds to Step S23. At this time, the operator can insert the treatment tool D10 into the channel 11 formed in the first bending portion 31 without making the channel 11 which is formed in the first bending portion 31 to be loosely bent.

In Step S23, the control portion 76 identifies position information about whether or not the position of the distal end of the rigid portion D12 is positioned at the distal end (a predetermined position) of the channel 11 formed in the first bending portion 31, based on an input signal sent from the position detection portion 79.

If the control portion 76 identifies that the rigid portion D12 of the treatment tool D10 is positioned at the distal end of the channel 11 formed in the first bending portion 31, the control portion 76 proceeds to Step S25 from Step S23.

In Step S25, the control portion 76 determines whether or not the radius of curvature of the axis C2 of the channel 11 formed in the second bending portion 32 is smaller than a predetermined value. When the second bending detection portion 72a receives an input signal sent from the position detection portion 79, the second bending detection portion 72a calculates the radius of curvature of the axis C2 of the channel 11 formed in the second bending portion 32 and a direction in which the second bending portion 32 is bent. The control portion 76 generates a second drive signal based on the result of the calculation of the radius of curvature of the axis C2 of the channel 11 formed in the second bending portion 32 that is performed by the second bending detection portion 72a.

In this case, since the radius of curvature of the axis C2 of the channel 11 formed in the second bending portion 32, which is calculated by the second bending detection portion 72a, is smaller than a predetermined value, the control portion 76 determines "YES" in Step S25 and proceeds to Step S27.

In Step S27, the bending detection portions 71a to 73a detect directions in which the bending portions 31 to 33 are bent. The bending detection portions 71a and 72a detect that the directions in which the bending portions 31 and 32 are bent in the first direction X1 from the axis C0 of the flexible tube portion 15, and the bending detection portion 73a detects that the third bending portion 33 is not bent.

The bending detection portions 71a to 73a send these detection results to the control portion 76. The control portion 76 proceeds to Step S29.

Figure 9:
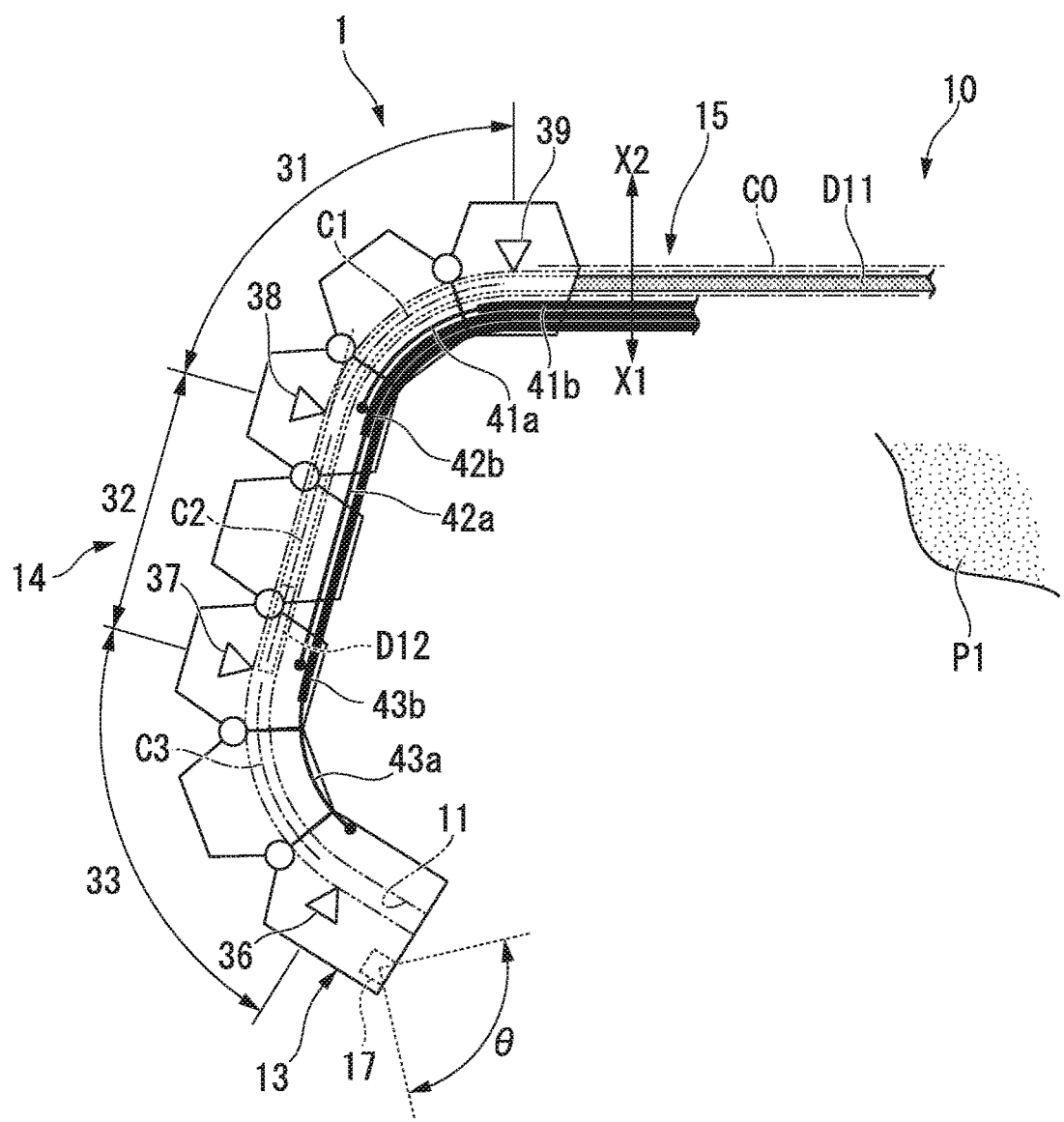
FIG. 9 is a view showing the action of the endoscope device according to the first embodiment of the invention.

In Step S29, as shown in FIG. 9, the control portion 76 releases the holding of the second operation-main wire 42a that is performed by the second wire drive motor 53, continues with the holding of the third operation-main wire 43a, and moves the first operation-main wire 41a to the proximal end side.

Since the holding of the second operation-main wire 42a, which is performed by the second wire drive motor 53, is released, the second bending portion 32 is easily bent in the first direction X1 or the second direction X2 from the axis C0 when the operator inserts the treatment tool D10. Accordingly, the second bending portion 32 becomes substantially straight along the shape of the rigid portion D12. The bending state of the bending portion 33 is being kept (the third bending portion 33 continues to be extremely bent) so that the radius of curvature of the axis C3 of the channel 11 formed in the third bending portion 33 is smaller than a predetermined value. The first bending portion 31 is controlled to allow the bending state of the first bending portion 31 to be changed (The first bending portion 31 is controlled to be extremely bent) from a substantially straight shape so that the radius of curvature of the axis C1 of the channel 11 formed in the first bending portion 31 is smaller than a predetermined value.

That is, the operator moves the rigid portion D12 to the channel 11, which is formed in the second bending portion 32, from the channel 11, which is formed in the first bending portion 31, in a state in which two bending portions (the first bending portion 31 and the third bending portion 33) among the three bending portions 31 to 33 are extremely bent. Accordingly, the field of view of the observation unit 17 shifting out of the treatment target P1 is prevented, so that the observation unit 17 faces the treatment target P1.

After this processing, the control portion 76 proceeds to Step S41.

If the control portion 76 determines in Step S25 that the radius of curvature of the axis C2 of the channel 11 formed in the second bending portion 32 is equal to or larger than a predetermined value (NO), the control portion 76 proceeds to Step S41. At this time, the operator can insert the treatment tool D10 into the channel 11 formed in the second bending portion 32 without making the channel 11 which is formed in the second bending portion 32 to be loosely bent.

In Step S41, the control portion 76 identifies position information about whether or not the position of the distal end of the rigid portion D12 is positioned at the distal end (a predetermined position) of the channel 11 formed in the second bending portion 32, based on an input signal sent from the position detection portion 79.

If the control portion 76 identifies that the rigid portion D12 of the treatment tool D10 is positioned at the distal end of the channel 11 formed in the second bending portion 32, the control portion 76 proceeds to Step S43 from Step S41.

In Step S43, the control portion 76 determines whether or not the radius of curvature of the axis C3 of the channel 11 formed in the third bending portion 33 is smaller than a predetermined value. In this case, since the radius of curvature of the axis C3 of the channel 11 formed in the third bending portion 33, which is calculated by the third bending detection portion 73a, is smaller than a predetermined value, the control portion 76 determines "YES" in Step S43 and proceeds to Step S45.

In Step S45, the bending detection portions 71a to 73a detect directions in which the bending portions 31 to 33 are bent. The bending detection portions 71a and 73a detect that the directions in which the bending portion 31 and the bending portion 33 are bent are the first direction X1 from the axis C0 of the flexible tube portion 15, and the second bending detection portion 72a detects that the second bending portion 32 is not bent.

The bending detection portions 71a to 73a send these detection results to the control portion 76. The control portion 76 proceeds to Step S47.

Figure 10:
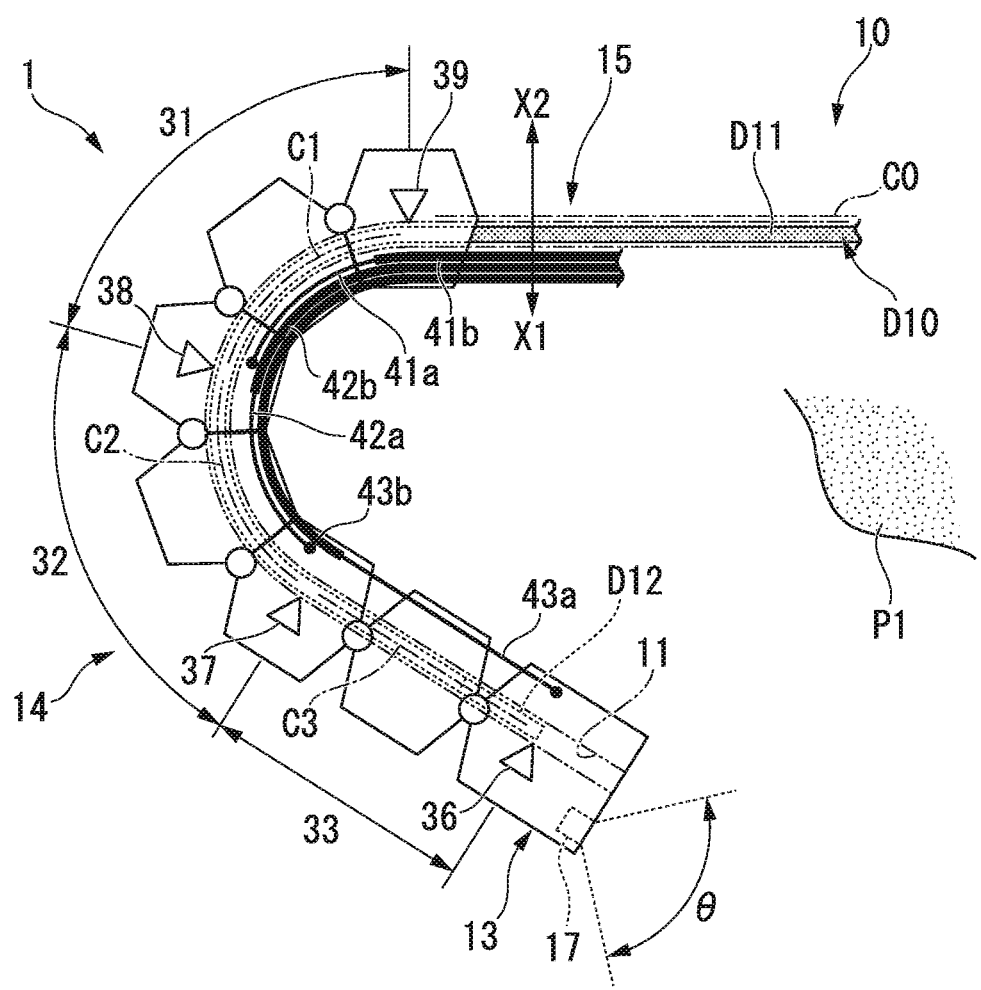
FIG. 10 is a view showing the action of the endoscope device according to the first embodiment of the invention.

In Step S47, as shown in FIG. 10, the control portion 76 releases the holding of the third operation-main wire 43a that is performed by the third wire drive motor 54, continues with the holding of the first operation-main wire 41a in a state in which the first operation-main wire 41a is moved to the proximal end side, and moves the second operation-main wire 42a to the proximal end side by the second wire drive motor 53.

Since the holding of the third operation-main wire 43a, which is performed by the third wire drive motor 54, is released, the third bending portion 33 is easily bent in the first direction X1 or the second direction X2 from the axis C0 when the operator inserts the treatment tool D10. Accordingly, the third bending portion 33 becomes substantially straight along the shape of the rigid portion D12.

The first bending portion 31 is controlled while the bending state of the first bending portion 31 is kept (while continuing to be extremely bent) so that the radius of curvature of the axis C1 of the channel 11 formed in the first bending portion 31 is smaller than a predetermined value. The second bending portion 32 is controlled to allow the bending state of the second bending portion 32 to be changed (The first bending portion 31 is controlled to be extremely bent) from a substantially straight shape so that the radius of curvature of the axis C2 of the channel 11 formed in the second bending portion 32 is smaller than a predetermined value.

After this processing, the control portion 76 proceeds to Step S49.

If the control portion 76 determines in Step S43 that the radius of curvature of the axis C3 of the channel 11 formed in the third bending portion 33 is equal to or larger than a predetermined value (NO), the control portion 76 proceeds to Step S49. At this time, the operator can insert the treatment tool D10 into the channel 11 formed in the third bending portion 33 without making the channel 11 which is formed in the third bending portion 33 to be loosely bent.

In Step S49, the control portion 76 identifies position information about whether or not the position of the distal end of the rigid portion D12 is positioned at the distal end (a predetermined position) of the channel 11 formed in the third bending portion 33, based on an input signal sent from the position detection portion 79.

If the position of the distal end of the rigid portion D12 is positioned at the distal end of the channel 11 formed in the third bending portion 33, the rigid portion D12 is disposed at a position D16 more distal than the third bending portion 33 as shown in FIG. 7.

After this processing, the control portion 76 proceeds to Step S51.

In Step S51, the control portion 76 switches the control mode to the manual operation mode from the automatic operation mode and proceeds to Step S53.

In Step S53, the control portion 76 continues with the holding of the first operation-main wire 41a, continues with the holding of the second operation-main wire 42a in a state in which the second operation-main wire 42a is moved to the proximal end side, and moves the third operation-main wire 43a to the proximal end side.

Since all the three bending portions 31 to 33 are extremely bent at this time, the field of view of the observation unit 17 is the same as the field of view that is obtained when the treatment tool D10 is not yet pushed into the channel 11.

The operator bends the bending portions 31 to 33 by appropriately operating the angle knob 59 in the manual operation mode. The operator pushes the treatment tool D10 into the channel 11 and allows the rigid portion D12 to protrude to the distal end side from the opening 11a of the distal end portion of the channel 11. The operator grasps the treatment target P1 with the rigid portion D12 and performs a treatment.

According to the endoscope device 1 of this embodiment, as described above, if the position detection portion 79 detects that the position of the distal end of the rigid portion D12 is positioned at the distal end of the channel 11 formed in the flexible tube portion 15 when all the three bending portions 31 to 33 are extremely bent in a J shape, the control portion 76 releases the holding of the first operation-main wire 41a and continues with the holding of the second operation-main wire 42a and the third operation-main wire 43a. When the fixing of the bent shape of the first bending portion 31 is released while a state in which the second bending portion 32 and the third bending portion 33 are extremely bent is kept, the operator can easily insert the rigid portion D12 of the treatment tool D10 into the channel 11 formed in the first bending portion 31.

At this time, all the three bending portions 31 to 33 do not have a substantially straight shape and two of the three bending portions 31 to 33 are extremely bent. Accordingly, the field of view of the observation unit 17 shifting out of the treatment target P1 can be prevented.

When the position detection portion 79 detects that the position of the distal end of the rigid portion D12 is positioned at the distal end of the channel 11 formed in the first bending portion 31, the control portion 76 releases the holding of the second operation-main wire 42a and moves the first operation-main wire 41a to the proximal end side.

When the rigid portion D12 is disposed in the channel 11 formed in the second bending portion 32 and the second bending portion 32 has a substantially straight shape, the operator can easily insert the rigid portion D12 of the treatment tool D10 into the channel 11 formed in the second bending portion 32 by extremely bending the first bending portion 31 and the third bending portion 33. Accordingly, the field of view of the observation unit 17 shifting out of the treatment target P1 can be prevented.

When the position detection portion 79 detects that the position of the distal end of the rigid portion D12 is positioned at the distal end of the channel 11 formed in the third bending portion 33, all the three bending portions 31 to 33 are made to be extremely bent. Accordingly, the field of view of the observation unit 17 can be made to be substantially the same as the field of view that is obtained when the treatment tool D10 is not yet inserted into the channel 11.

In the present embodiment, modification examples having the structures to be described below can be used as the position sensors 36 to 39.

Figure 11:
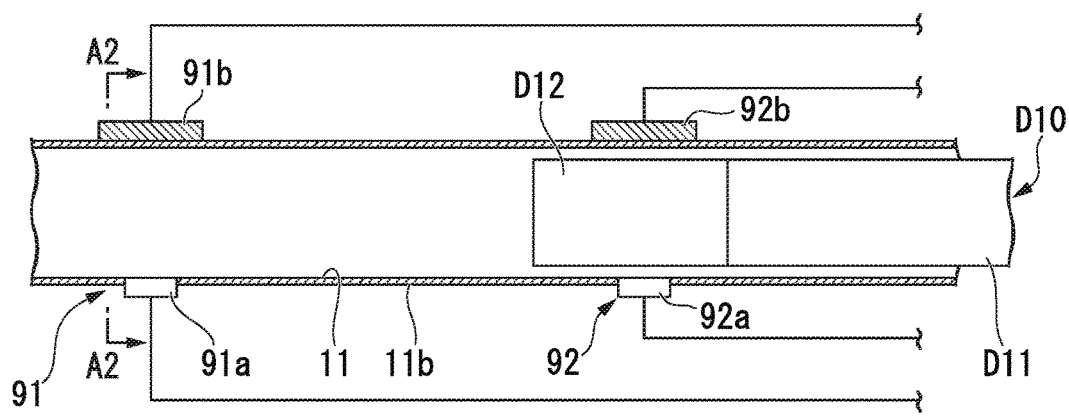
FIG. 11 is a side sectional view showing a position sensor of a modification example of the endoscope device according to the first embodiment of the invention.
Figure 12:
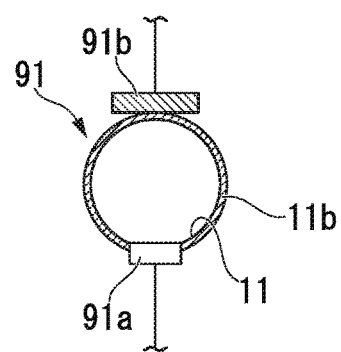
FIG. 12 is a cross-sectional view taken along line A2-A2 of FIG. 11.

A third position sensor 91 shown in FIGS. 11 and 12 includes a light emitting portion 91a that emits light and a light receiving portion 91b that detects the light emitted from the light emitting portion 91a. A publicly known light emitting diode can be used as the light emitting portion 91a, and a photodiode can be used as the light receiving portion 91b.

The light emitting portion 91a and the light receiving portion 91b are mounted on the inner peripheral surface of a tube 11b, which forms a channel 11, so as to face each other. In this example, the light emitting portion 91a always emits light toward the light receiving portion 91b after the endoscope device 1 is started up.

The action of the third position sensor 91 will be described using a fourth position sensor 92.

As in the case of the third position sensor 91, the fourth position sensor 92 includes a light emitting portion 92a and a light receiving portion 92b.

When the rigid portion D12 of the treatment tool D10 enters a space between the light emitting portion 92a and the light receiving portion 92b, the light receiving portion 92b cannot detect the light that is emitted from the light emitting portion 92a and has been detected up to that time. Accordingly, whether or not the position of the distal end of the rigid portion D12 corresponds to the position of the fourth position sensor 92 is identified.

Figure 13:
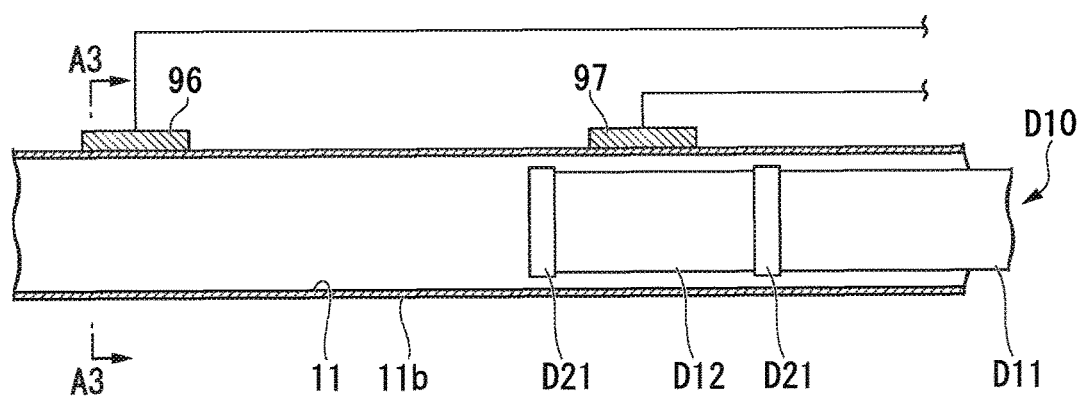
FIG. 13 is a side sectional view showing a position sensor of a modification example of the endoscope device according to the first embodiment of the invention.
Figure 14:
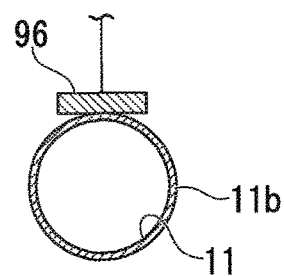
FIG. 14 is a cross-sectional view taken along line A3-A3 of FIG. 13.

Another modification example of the position sensor is shown in FIGS. 13 and 14. Each of a third position sensor 96 and a fourth position sensor 97, which are shown in FIGS. 13 and 14, includes a hall element. In the present modification example, a pair of ring-shaped permanent magnets D21 are provided on the outer peripheral surface of a rigid portion D12 of a treatment tool D10.

When the permanent magnet D21 provided on the rigid portion D12 approaches the fourth position sensor 97, the hall element detects a change in a magnetic field. Accordingly, whether or not the position of the distal end of the rigid portion D12 corresponds to the position of the fourth position sensor 92 is identified.

Figure 15:
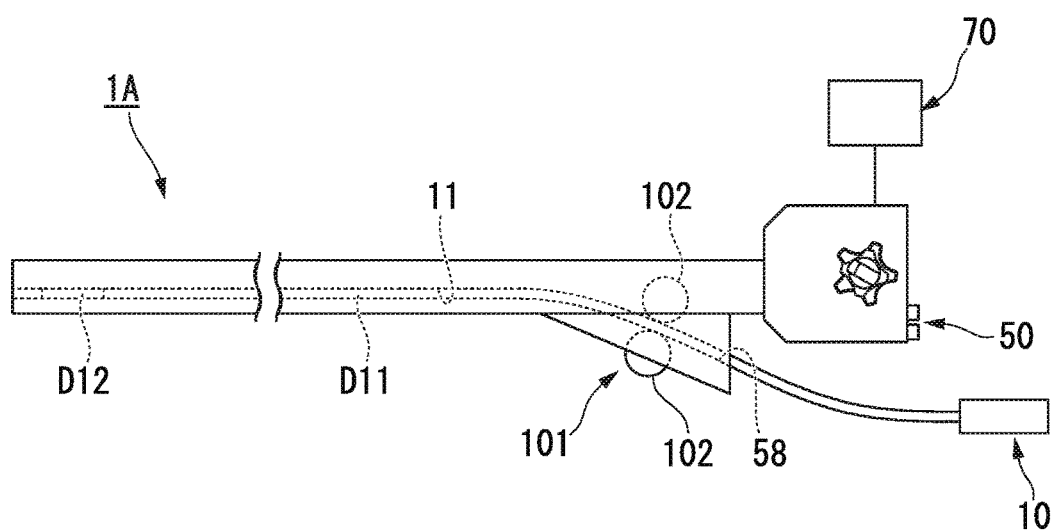
FIG. 15 is a view schematically showing a modification example of the endoscope device according to the first embodiment of the invention.

Another modification example of the position sensor is shown in FIG. 15. A position sensor 101 of an endoscope device 1A shown in FIG. 15 is a sensor that detects the position of a rigid portion D12 of a treatment tool D10 inserted into a channel 11 from the lengths of the rigid portion D12 and a treatment tool-insertion portion D11 of the treatment tool D10 inserted into the channel 11.

That is, the position sensor 101 includes a pair of rollers 102 that are provided so that a portion of the rollers 102 protrude from the inner peripheral surface of a proximal end portion of the channel 11, an arithmetic element (not shown), a memory (not shown), and the like.

The pair of rollers 102 are rotated according to the lengths of the rigid portion D12 and the treatment tool-insertion portion D11 that are inserted into the channel 11. The positions of the bending portions 31 to 33 in the longitudinal direction of the channel 11, the length of the rigid portion D12, and the like are stored in the memory.

The arithmetic element calculates the lengths of the rigid portion D12 and the treatment tool-insertion portion D11 of the treatment tool D10 inserted into the channel 11 from the number of revolution of the rollers 102. Then, the arithmetic element calculates a positional relationship between each of the bending portions 31 to 33 and the distal end of the rigid portion D12, and the like.

Not only the position of the distal end of the rigid portion D12 but also the position of the proximal end of the rigid portion D12 can be identified in the endoscope device 1A having this structure.

In a case in which the treatment target P1 is to be incised, or the like while a treatment for a mucous membrane of the first embodiment is performed using the endoscope device 1A, an operator replaces the treatment tool D10, which is a pair of biopsy forceps, with a high-frequency knife.

In this case, the treatment tool D10 is pulled back from the channel 11 in an order reverse to an order where the treatment tool D10 is pushed into the channel 11.

The outline of this order will be described. When an operator pulls back the treatment tool D10 and it is identified that the position of the proximal end of the rigid portion D12 is positioned at the distal end of the channel 11 formed in the third bending portion 33, the control mode is switched to the automatic operation mode from the manual operation mode. In a case in which the third bending portion 33 is extremely bent (the radius of curvature of the axis is smaller than a predetermined value), the control portion 76 releases the holding of the third operation-main wire 43a and continues with the holding of the first operation-main wire 41a and the second operation-main wire 42a.

When the rigid portion D12 is inserted into the channel 11 formed in the third bending portion 33 and it is identified that the position of the proximal end of the rigid portion D12 is positioned at the distal end of the channel 11 formed in the second bending portion 32, control is performed as described below. In a case in which the second bending portion 32 is extremely bent, the control portion 76 releases the holding of the second operation-main wire 42a, continues with the holding of the first operation-main wire 41a, and moves the third operation-main wire 43a to the proximal end side.

When the rigid portion D12 enters the channel 11 formed in the second bending portion 32 and it is identified that the position of the proximal end of the rigid portion D12 is positioned at the distal end of the channel 11 formed in the first bending portion 31, control is performed as described below. In a case in which the first bending portion 31 is extremely bent, an operator releases the holding of the first operation-main wire 41a, continues with the holding of the third operation-main wire 43a, and moves the second operation-main wire 42a to the proximal end side.

When the first bending portion 31 is loosely bent and the rigid portion D12 enters the channel 11 formed in the first bending portion 31, the rigid portion D12 is pulled back to the proximal end side from the first bending portion 31 and is pulled out of the channel 11.

After that, the operator replaces the treatment tool D10 with a new treatment tool and inserts the new treatment tool into the channel 11 by the above-mentioned method. The operator incises the treatment target P1 by using the treatment tool that is newly inserted.

In the present embodiment, a table representing a correspondence relationship between the rotation angle of the rotating shafts of the wire drive motors 52 to 54 from reference positions and the radius of curvature of the axis C1 of the channel 11, which is formed in the first bending portion 31, may not be stored in the memories of the bending calculation portions 71 to 73, and the control portion may perform image processing to be described below.

The control portion calculates a displacement between an image of the treatment target P1 and an image, which is taken when the field of view of the observation unit 17 deviates from the treatment target P1, and a vector. Then, the control portion 76 calculates the rotation angles of the rotating shafts of the wire drive motors 52 to 54 based on the calculated displacement and the calculated vector.

Second Embodiment

Next, a second embodiment of the invention will be described with reference to FIGS. 16 to 18. However, the same portions as the first embodiment will be denoted by the same reference numerals and the description thereof will be omitted, and only a difference between the first and second embodiments will be described.

Figure 16:
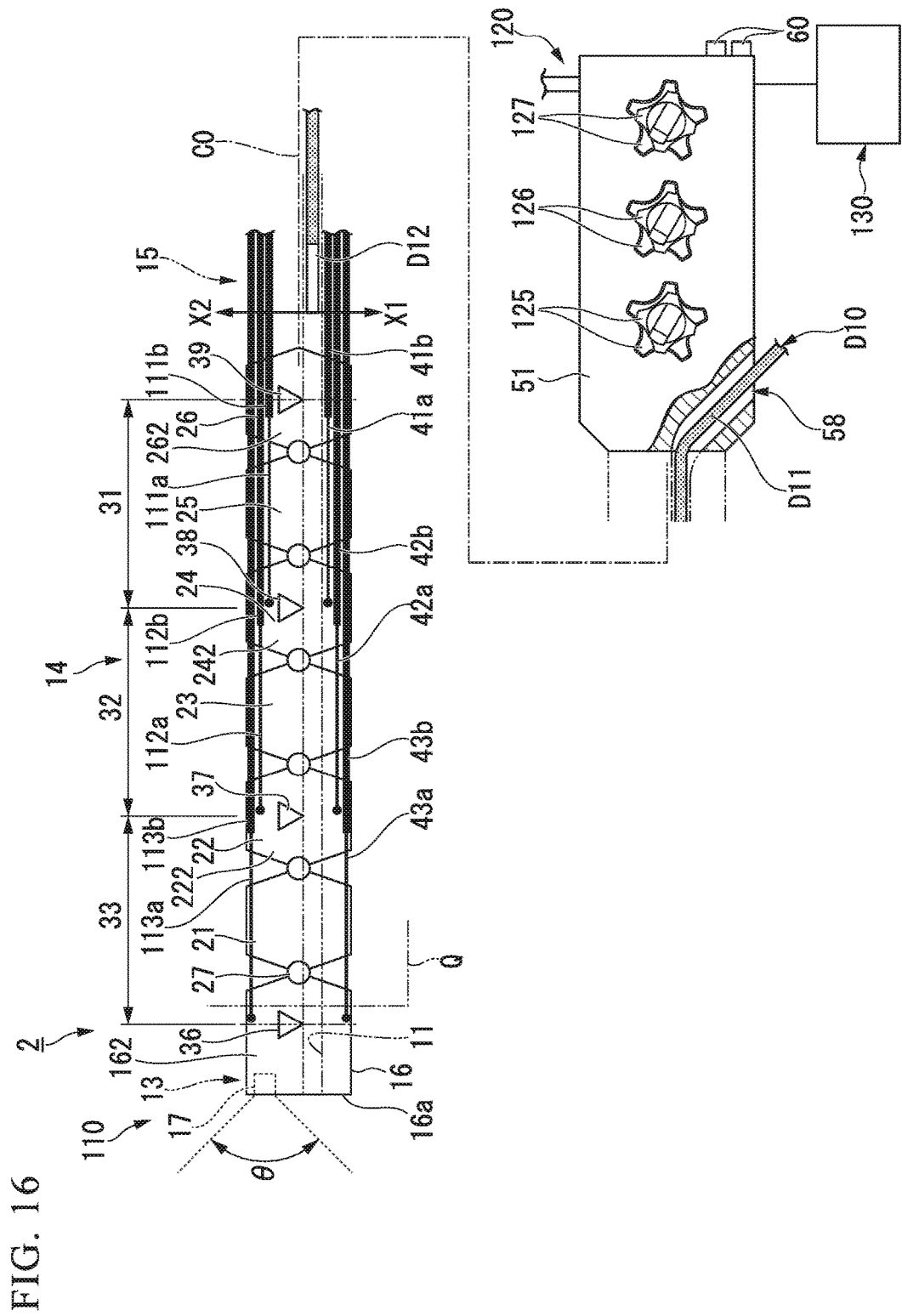
FIG. 16 is a view showing an endoscope device according to a second embodiment of the invention.
Figure 17:
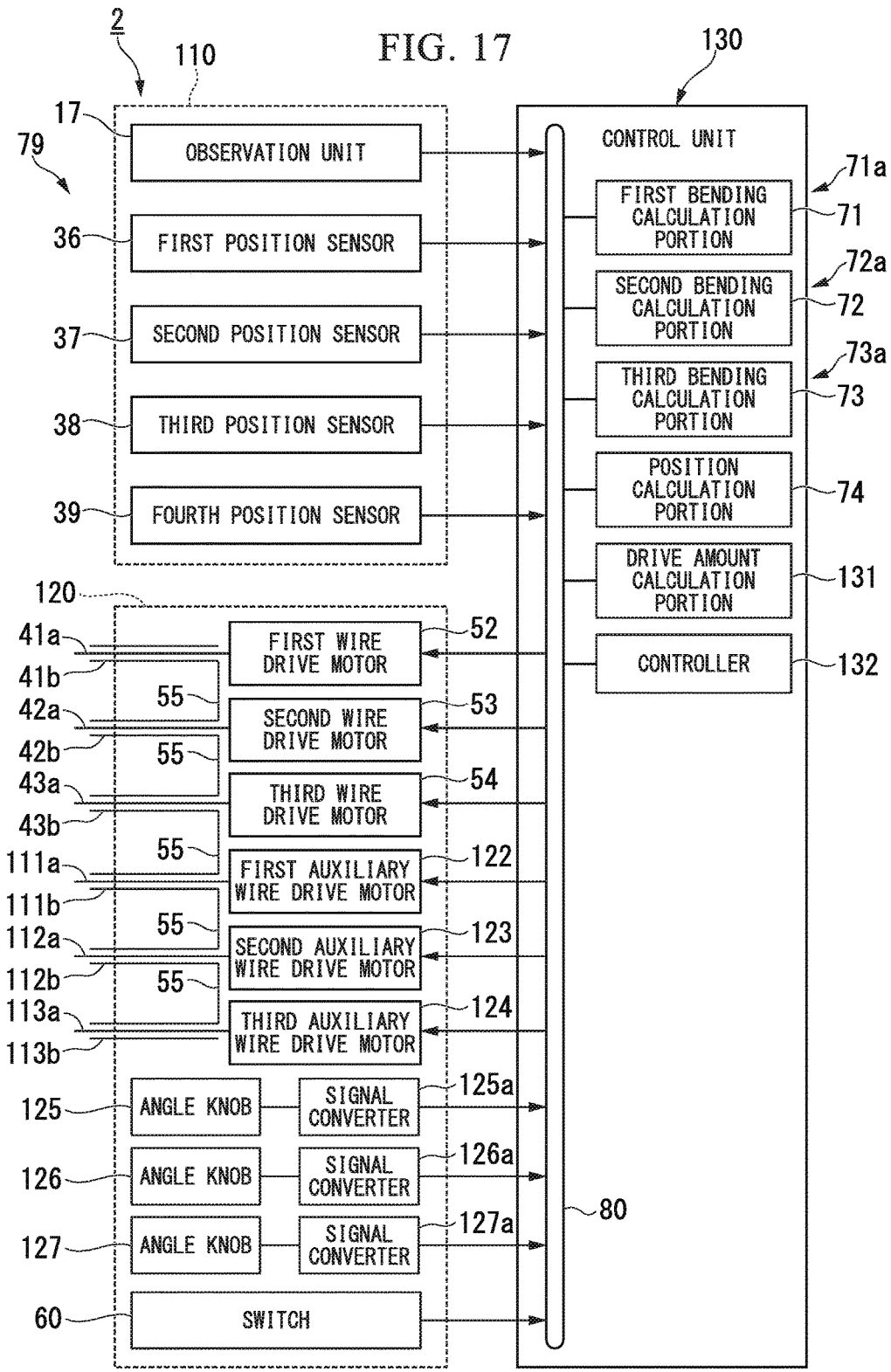
FIG. 17 is a block diagram of the endoscope device according to the second embodiment of the invention.
Figure 18:
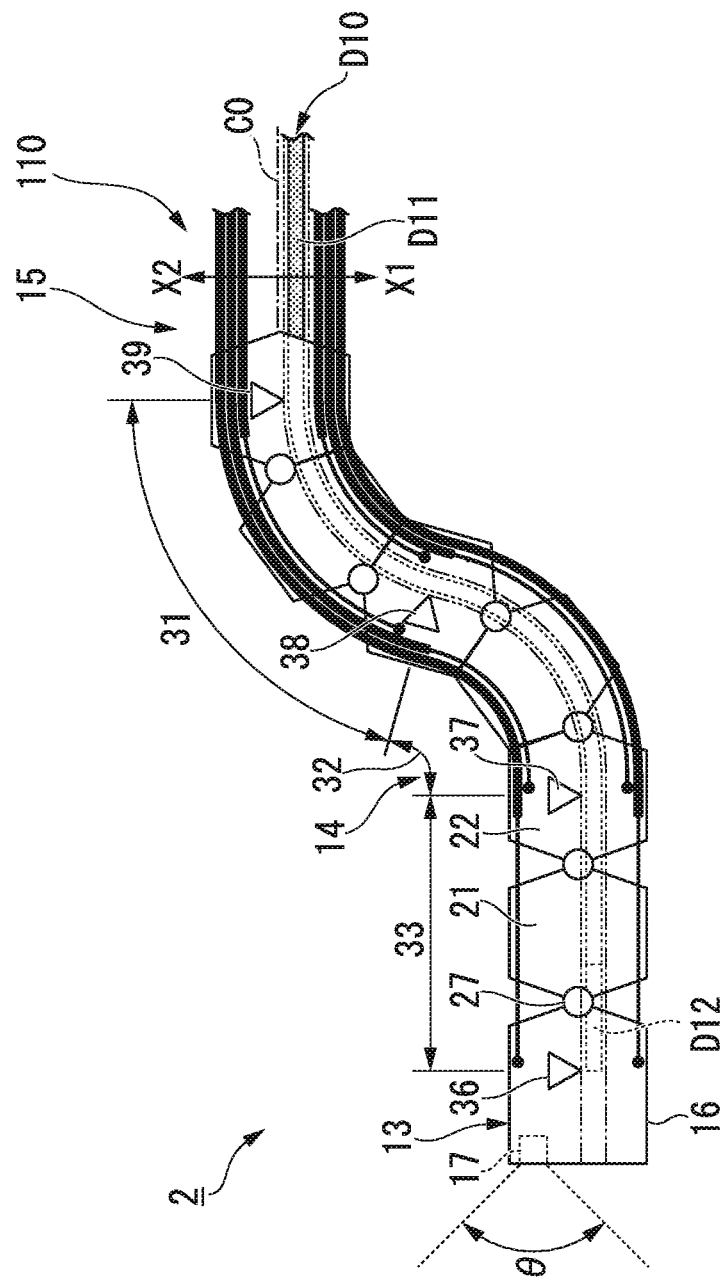
FIG. 18 is a view showing the action of the endoscope device according to the second embodiment of the invention.

As shown in FIGS. 16 and 17, an endoscope device 2 of this embodiment includes an insertion portion 110 that is made of a flexible material and is formed in a columnar shape, an operation portion 120 that is provided at a proximal end portion of the insertion portion 110, and a control unit 130 that is connected to the operation portion 120.

The insertion portion 110 includes a first operation-auxiliary wire (a first operation wire) 111a, a coil sheath 111b, a second operation-auxiliary wire (a second operation wire) 112a, a coil sheath 112b, a third operation-auxiliary wire 113a, and a coil sheath 113b in addition to the respective components of the insertion portion 10.

A distal end portion of the first operation-auxiliary wire 111a is connected to a second side portion 242, which is at the proximal end side, of the joint ring 24 by welding or the like. The first operation-auxiliary wire 111a is inserted into the coil sheath 111b. A distal end portion of the coil sheath 111b is connected to a second side portion 262 of the joint ring 26 by welding or the like.

When the first operation-auxiliary wire 111a is moved (pulled back) to the proximal end side from the coil sheath 111b, the first bending portion 31 is bent in (toward) the second direction X2 from the axis C0. When the first operation-auxiliary wire 111a is moved (pushed) to the distal end side from the coil sheath 111b, the first bending portion 31 is bent in (toward) the first direction X1 from the axis C0.

The second operation-auxiliary wire 112a and the third operation-auxiliary wire 113a have the same structure as the structure of the first operation-auxiliary wire 111a. The coil sheath 112b and the coil sheath 113b have the same structure as the structure of the coil sheath 111b.

Specifically, a distal end portion of the second operation-auxiliary wire 112a is connected to a second side portion 222, which is at the proximal end side, of the joint ring 22. The second operation-auxiliary wire 112a is inserted into the coil sheath 112b. A distal end portion of the coil sheath 112b is connected to the second side portion 242 of the joint ring 24. When the second operation-auxiliary wire 112a is pulled back from the coil sheath 112b, the second bending portion 32 is bent in the second direction X2 from the axis C0.

A distal end portion of the third operation-auxiliary wire 113a is connected to a second side portion 162, which is at the proximal end side, of the support member 16. The third operation-auxiliary wire 113a is inserted into the coil sheath 113b. A distal end portion of the coil sheath 113b is connected to the second side portion 242 of the joint ring 24. When the third operation-auxiliary wire 113a is pulled back from the coil sheath 113b, the first bending portion 31 is bent in the second direction X2 from the axis C0.

As shown in FIGS. 16 and 17, the operation portion 120 includes a first auxiliary wire drive motor (a first drive portion) 122, a second auxiliary wire drive motor (a second drive portion) 123, a third auxiliary wire drive motor 124, and three angle knobs 125 to 127, instead of the angle knob 59 of the operation portion 50.

The auxiliary wire drive motors 122 to 124 are fixed to the support members 55.

A proximal end portion of the first operation-auxiliary wire 111a is connected to a rotating shaft (not shown) of the first auxiliary wire drive motor 122. A proximal end portion of the coil sheath 111b into which the first operation-auxiliary wire 111a is inserted is fixed to the support member 55.

Likewise, a proximal end portion of the second operation-auxiliary wire 112a is connected to a rotating shaft (not shown) of the second auxiliary wire drive motor 123. A proximal end portion of the coil sheath 112b into which the second operation-auxiliary wire 112a is inserted is fixed to the support member 55. A proximal end portion of the third operation-auxiliary wire 113a is connected to a rotating shaft (not shown) of the third auxiliary wire drive motor 124. A proximal end portion of the coil sheath 113b into which the third operation-auxiliary wire 113a is inserted is fixed to the support member 55.

When power is supplied to the first auxiliary wire drive motor 122 and the rotating shaft of the first auxiliary wire drive motor 122 is rotated in one direction, the first operation-auxiliary wire 111a is pulled back from the coil sheath 111b. Accordingly, the first bending portion 31 is bent in the second direction X2 from the axis C0.

Likewise, when power is supplied to the second auxiliary wire drive motor 123 and the rotating shaft of the second auxiliary wire drive motor 123 is rotated in one direction, the second operation-auxiliary wire 112a is pulled back from the coil sheath 112b. Accordingly, the second bending portion 32 is bent in the second direction X2 from the axis C0. When power is supplied to the third auxiliary wire drive motor 124 and the rotating shaft of the third auxiliary wire drive motor 124 is rotated in one direction, the third operation-auxiliary wire 113a is pulled back from the coil sheath 113b. Accordingly, the third bending portion 33 is bent in the second direction X2 from the axis C0.

A potentiometer (not shown) is built in each of the auxiliary wire drive motors 122 to 124. The rotation angle of each of the rotating shafts of the wire drive motors 122 to 124 from a reference position is detected by the potentiometer. The potentiometers convert detection results into signals and send the signals to the control unit 130. The potentiometers may be provided outside the auxiliary wire drive motors 122 to 124.

The three angle knobs 125, 126, and 127 are operation portions that are used to operate the first bending portion 31, the second bending portion 32, and the third bending portion 33, respectively, when the control mode is the manual operation mode.

Signal converters 125a, 126a, and 127a, which convert the rotation angle of the angle knobs 125, 126, and 127 into signals, are connected to the angle knobs 125, 126, and 127 (see FIG. 17).

The control unit 130 includes a drive amount calculation portion 131 and a control portion 132 instead of the drive amount calculation portion 75 and the control portion 76 of the control unit 70 of the first embodiment.

The drive amount calculation portion 131 and the control portion 132 are adapted to correspond to added components that are the operation-auxiliary wires 111a to 113a and the auxiliary wire drive motors 122 to 124.

The endoscope device 2 having the above-mentioned structure can perform the same operation as the operation of the endoscope device 1 of the first embodiment.

The action of the endoscope device 2 is different from that of the endoscope device 1 in terms of the following two points.

First, generally, a wire can more efficiently transmit a pulling force than a pushing force. Accordingly, for example, the first operation-main wire 41a is operated so as to be pulled back in a case in which the first bending portion 31 is to be bent in the first direction X1 from the axis C0. At this time, the first operation-auxiliary wire 111a is pushed. The first operation-auxiliary wire 111a is operated so as to be pulled back in a case in which the first bending portion 31 is to be bent in the second direction X2 from the axis C0. At this time, the first operation-main wire 41a is pushed. That is, the first bending portion 31 can be bent in the first direction X1 or the second direction X2 by an operation for pulling back the first operation-main wire 41a or the first operation-auxiliary wire 111a.

Accordingly, since the operation-auxiliary wires 111a to 113a are provided, the endoscope device 2 can be more efficiently operated.

Second, the bending portions 31 to 33 can be operated so as to be independently bent in the manual operation mode. Accordingly, for example, as shown in FIG. 18, the second bending portion 32 can be bent in the second direction X2 from the axis C0 and the first bending portion 31 can be bent in the first direction X1 from the axis C0 in a state in which the third bending portion 33 is substantially straight.

A state in which at least one of the bending portions 31 to 33 is bent in the first direction X1 from the axis C0 and at least one thereof is bent in the second direction X2 from the axis C0 in this way will be referred to as "the bending portions 31 to 33 are bent in an S shape" hereinafter.

Third Embodiment

Next, a third embodiment of the invention will be described with reference to FIGS. 19 to 28. However, the same portions as the above-mentioned embodiment will be denoted by the same reference numerals and the description thereof will be omitted, and only a difference between the third embodiment and the above-mentioned embodiment will be described. A shape is more schematically shown in FIGS. 19 to 28.

Figure 19:
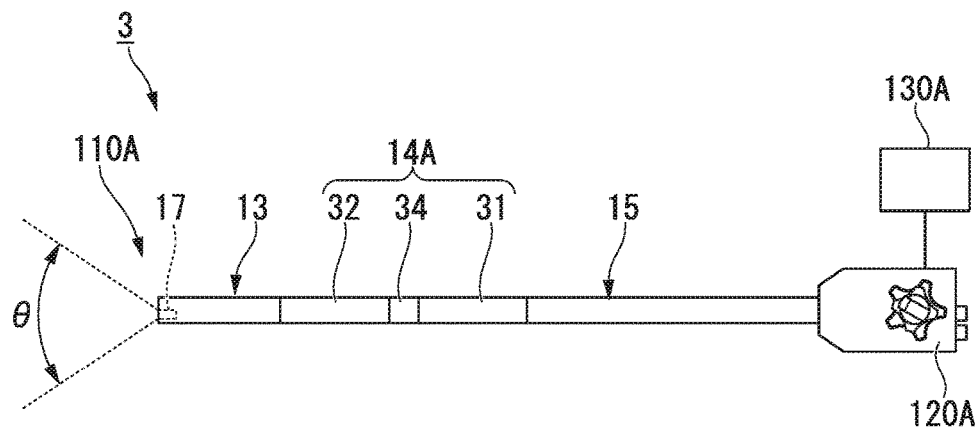
FIG. 19 is a view showing an endoscope device according to a third embodiment of the invention.

As shown in FIG. 19, an endoscope device 3 of this embodiment includes an insertion portion 110A that is made of a flexible material and is formed in a columnar shape, an operation portion 120A that is provided at a proximal end portion of the insertion portion 110A, and a control unit 130A that is connected to the operation portion 120A.

The insertion portion 110A includes a multi-stage bending portion 14A instead of the multi-stage bending portion 14 of the insertion portion 110 of the second embodiment. The multi-stage bending portion 14A does not include the third bending portion 33, and includes a first bending portion 31, a straight tube portion 34 that is provided more distal than the first bending portion 31, and a second bending portion 32 that is provided more distal than the straight tube portion 34.

The straight tube portion 34 is made of a rigid material and is formed in a cylindrical shape as in the case of the joint ring 21. Since the straight tube portion 34 is made of a rigid material, the direction and position of the second bending portion 32 relative to the first bending portion 31 are constant.

The insertion portion 110A does not include the third operation-main wire 43a, the coil sheath 43b, the third operation-auxiliary wire 113a, and the coil sheath 113b.

The operation portion 120A has the structure of the operation portion 120 of the second embodiment from which the third wire drive motor 54 and the third auxiliary wire drive motor 124 are excluded.

The control unit 130A has the structure of the control unit 130 of the second embodiment from which the third bending detection portion 73a is excluded.

Next, the action of the endoscope device 3 having the above-mentioned structure will be described. Description will be made while focusing on directions in which the first bending portion 31 and the second bending portion 32 are bent and the radius of curvature of the axis of the channel 11 formed in the bending portions 31 and 32. For convenience of description, the distal end of the rigid portion D12 of the treatment tool D10 is shown in FIGS. 21 to 28 by a circle E that is shown by a dotted line.

Figure 20:
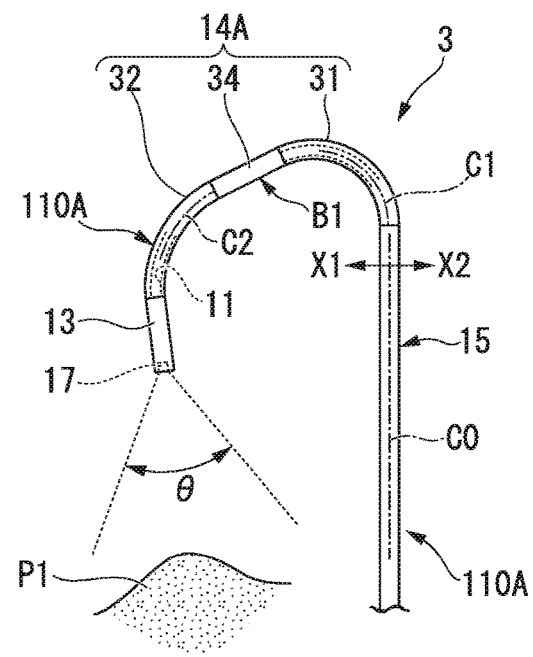
FIG. 20 is a view showing the action of the endoscope device according to the third embodiment of the invention.

As shown in FIG. 20, an operator makes the distal end surface of the insertion portion 110A face a treatment target P1 so that the treatment target P1 is within the angle θ of view.

At this time, a direction in which the channel 11 formed in the first bending portion 31 is bent is a first direction X1 from an axis C0 of the flexible tube portion 15, and a direction, in which the channel 11 formed in the second bending portion 32 is bent and which is detected by the second bending detection portion 72a, is a first direction X1 from the axis C0. That is, the bending portions 31 and 32 are bent in a J shape.

The radius of curvature of the axis C1 of the channel 11 formed in the first bending portion 31 is smaller than the above-mentioned predetermined value. The bent shape of the insertion portion 110A at this time is defined as a bent shape B1.

Figure 21:
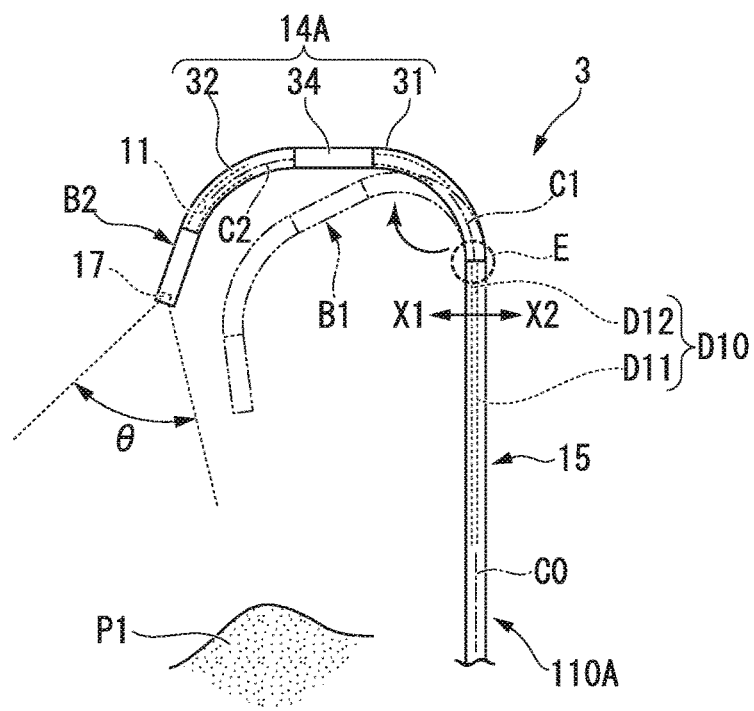
FIG. 21 is a view showing the action of the endoscope device according to the third embodiment of the invention.

When the control portion 132 identifies that the position of the distal end of the rigid portion D12 is positioned at the distal end of the channel 11 formed in the flexible tube portion 15 as shown in FIG. 21 by the position detection portion 79, the first bending detection portion 71a detects that the radius of curvature of the axis C1 of the channel 11 formed in the first bending portion 31 is smaller than the predetermined value. The control portion 132 releases the holding of the first operation-main wire 41a by the first wire drive motor 52, and moves the first operation-auxiliary wire 111a to the proximal end side. Accordingly, the control portion 132 makes the first bending portion 31 to be loosely bent in the first direction X1 and makes the radius of curvature of the axis C1 of the channel 11, which is formed in the first bending portion 31, become equal to or larger than the predetermined value. The bent shape of the insertion portion 110A at this time is defined as a bent shape B2.

The bent shape B1 of the insertion portion 100A of FIG. 20 is shown in FIG. 21 by a two-dot chain line.

However, there is a possibility that the treatment target P1 may deviate from the angle θ of view of the observation unit 17 when the first bending portion 31 is merely made to be loosely bent in the first direction X1 from the axis C0.

Figure 22:
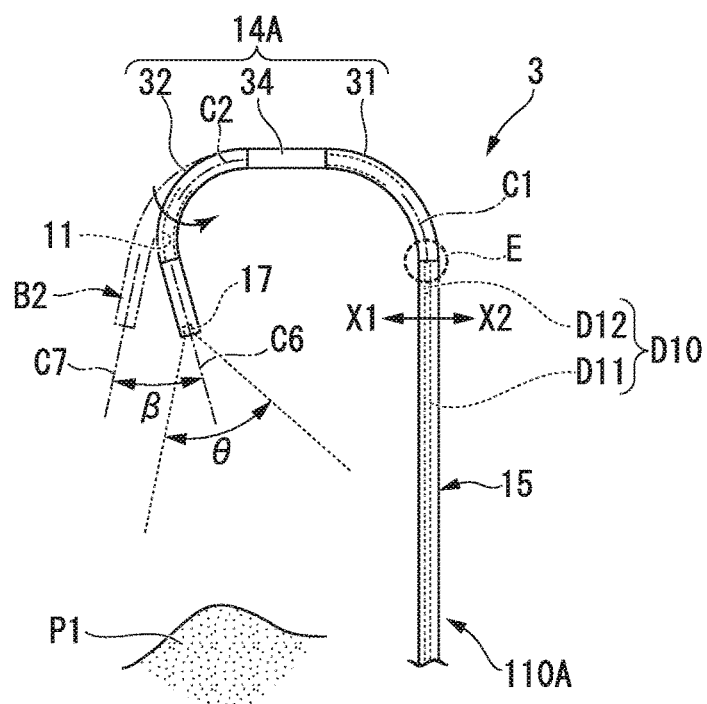
FIG. 22 is a view showing the action of the endoscope device according to the third embodiment of the invention.

Accordingly, the control portion 132 more extremely bends the second bending portion 32 in the first direction X1 from the axis C0 (reduces the radius of curvature of the center line of the second bending portion 32) by making the first bending portion 31 to be loosely bent and further moving the second operation-main wire 42a to the proximal end side as shown in FIG. 22. The bent shape B2 of the insertion portion 110A of FIG. 21 is shown in FIG. 22 by a two-dot chain line.

The degree of the extreme bending of the second bending portion 32 is controlled so that an angle β between an optical axis C6 of the observation unit 17, which is obtained when the treatment target P1 is positioned at the center of the angle θ of view, and an optical axis C7 of the observation unit 17, which is obtained when the first bending portion 31 is loosely bent, is equal to or smaller than the value (θ/2) of the half of the angle θ of view. When the degree of the extreme bending of the second bending portion 32 is controlled in this way, the treatment target P1 can be made to be within the angle θ of view even though the bending states of the bending portions 31 and 32 are changed.

When the first bending portion 31 is made to be loosely bent in the first direction X1 and the bending of the second bending portion 32 in the first direction X1 is made to be extreme, it is easy to insert the rigid portion D12 of the treatment tool D10 into the channel 11 formed in the first bending portion 31 while preventing the treatment target P1 from shifting out of the angle θ of view of the observation unit 17.

When the position detection portion 79 identifies that the position of the distal end of the rigid portion D12 is positioned at the distal end of the channel 11 formed in the straight tube portion 34 (the first bending portion 31) and the second bending detection portion 72a detects that the radius of curvature of the axis C2 of the channel 11 formed in the second bending portion 32 is smaller than the predetermined value, the control portion 132 performs the following processing.

Figure 23:
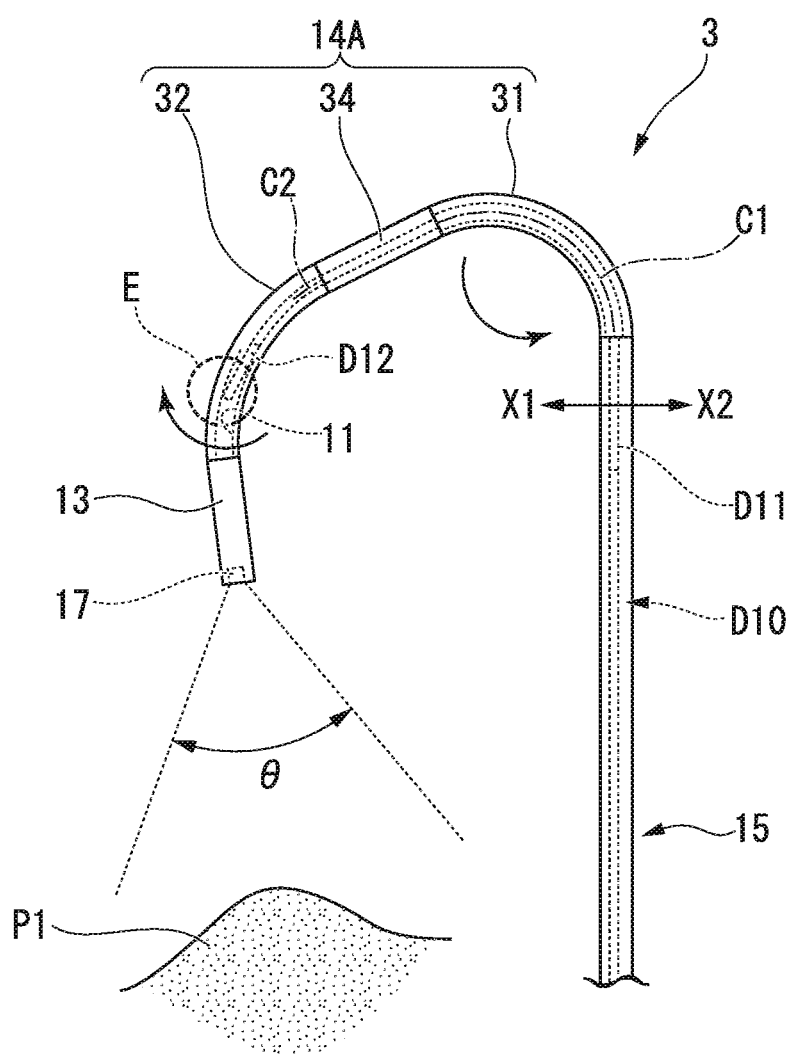
FIG. 23 is a view showing the action of the endoscope device according to the third embodiment of the invention.

That is, the control portion 132 releases the holding of the second operation-main wire 42a, which is performed by the second wire drive motor 53, and moves the second operation-auxiliary wire 112a to the proximal end side by the second auxiliary wire drive motor 123. Accordingly, the control portion 132 controls the radius of curvature of the axis C2 of the channel 11, which is formed in the second bending portion 32, to the predetermined value or more, and makes the second bending portion 32 to be loosely bent in the first direction X1 as shown in FIG. 23.

However, there is a possibility that the treatment target P1 may deviate from the angle θ of view of the observation unit 17 when the second bending portion 32 is merely made to be loosely bent in the first direction X1.

Accordingly, the control portion 132 makes the first bending portion 31 to be loosely bent in the first direction X1 and moves the first operation-main wire 41a to the proximal end side by the first wire drive motor 52. Therefore, the control portion 132 makes the bending of the first bending portion 31 to be extreme in the first direction X1 from the axis C0 by more extremely bending the first bending portion 31 in the first direction X1 from the axis C0.

When the second bending portion 32 is made to be loosely bent in the first direction X1 and the first bending portion 31 is made to be extremely bent in the first direction X1, it is easy to insert the rigid portion D12 of the treatment tool D10 into the channel 11 formed in the second bending portion 32 while preventing the treatment target P1 from shifting out of the angle $\theta$ of view of the observation unit 17.

Figure 24:
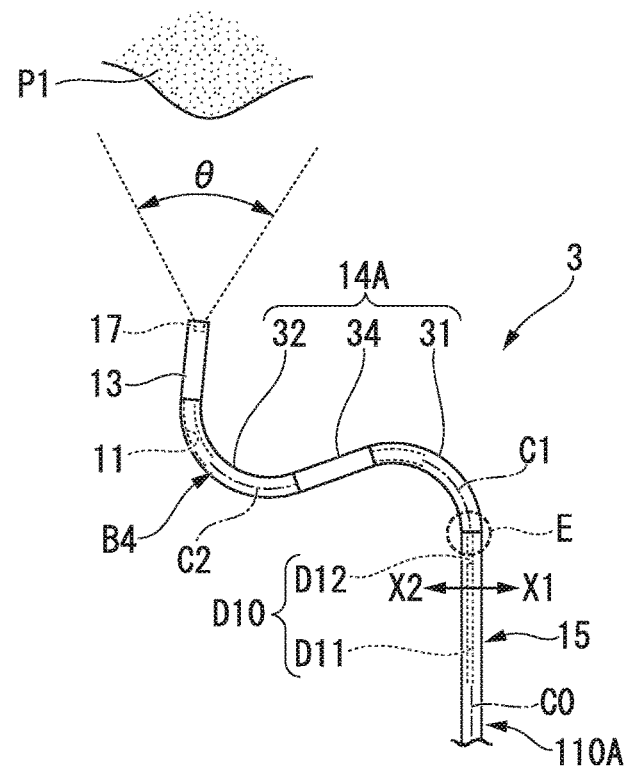
FIG. 24 is a view showing the action of the endoscope device according to the third embodiment of the invention.

Next, the action of the endoscope device 3 having the above-mentioned structure will be described in a case in which the bending portions 31 and 32 are bent in an S shape when the distal end surface of the insertion portion 10 is made to face the treatment target P1 so that the treatment target P1 is within the angle $\theta$ of view as shown in FIG. 24. In more detail, this case is a case where a direction in which the channel 11 formed in the second bending portion 32 is bent corresponds to the first direction X1 from the axis C0 of the flexible tube portion 15 and a direction in which the channel 11 formed in the first bending portion 31 is bent is the second direction X2 from the axis C0.

At this time, the radius of curvature of the axis C1 of the channel 11 formed in the first bending portion 31 is smaller than the above-mentioned predetermined value.

When the control portion 132 identifies that the position of the distal end of the rigid portion D12 is positioned at the distal end of the channel 11 formed in the flexible tube portion 15 as shown in FIG. 24 by the position detection portion 79, the control portion 132 detects that the radius of curvature of the axis C1 of the channel 11 formed in the first bending portion 31 is smaller than the predetermined value, by the first bending detection portion 71a. The bending detection portions 71a and 72a detect directions in which the channel 11 formed in the first bending portions 31 and 32 is bent. The bent shape of the insertion portion 110A at this time is defined as a bent shape B4.

Figure 25:
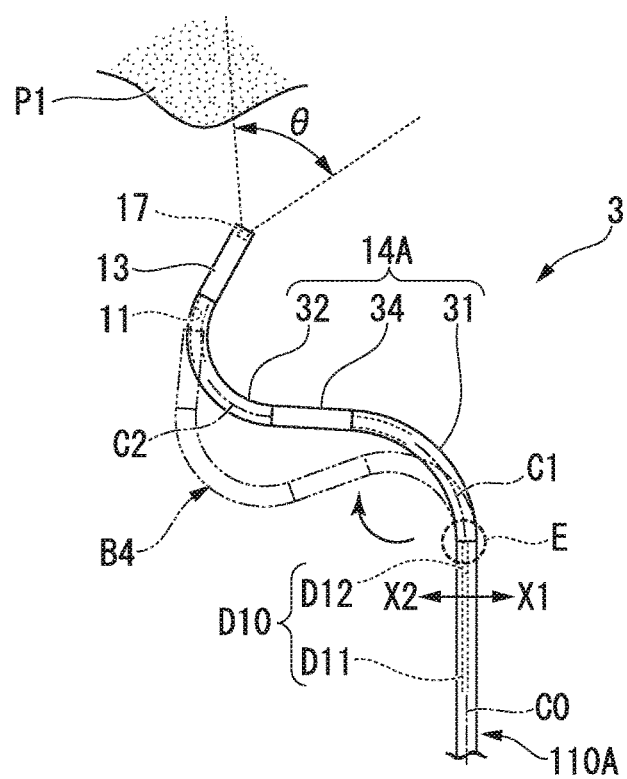
FIG. 25 is a view showing the action of the endoscope device according to the third embodiment of the invention.

At this time, the control portion 132 releases the holding of the first operation-auxiliary wire 111a, which is performed by the first auxiliary wire drive motor 122, and moves the first operation-main wire 41a to the proximal end side by the first wire drive motor 52. Accordingly, the control portion 132 makes the first bending portion 31 in the second direction X2 from the axis C0 be loosely bent (increases the radius of curvature of the center line of the first bending portion 31) as shown in FIG. 25 and makes the radius of curvature of the axis C1 of the channel 11, which is formed in the first bending portion 31, become equal to or larger than the predetermined value. The bent shape B4 of the insertion portion 110A of FIG. 24 is shown in FIG. 25 by a two-dot chain line.

However, there is a possibility that the treatment target P1 may deviate from the angle $\theta$ of view of the observation unit 17 when the first bending portion 31 in the second direction X2 from the axis C0 is merely made to be loosely bent.

Figure 26:
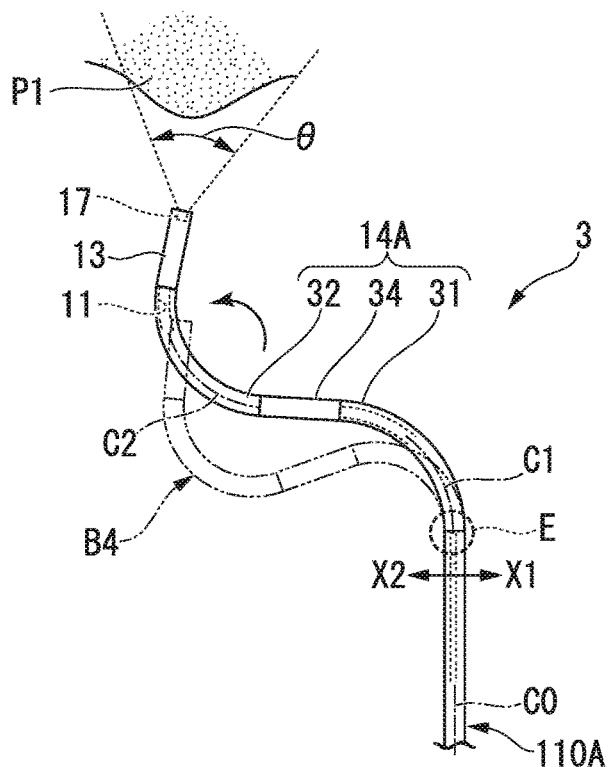
FIG. 26 is a view showing the action of the endoscope device according to the third embodiment of the invention.

Accordingly, the control portion 132 makes the first bending portion 31 to be loosely bent, while makes the second bending portion 32 to be loosely bent in the first direction X1 from the axis C0, as shown in FIG. 26, by releasing the holding of the second operation-main wire 42a by the second wire drive motor 53 and moving the second operation-auxiliary wire 112a to the proximal end side by the second auxiliary wire drive motor 123. The bent shape B4 of the insertion portion 110A of FIG. 24 is shown in FIG. 26 by a two-dot chain line.

When the first bending portion 31 in the second direction X2 is made to be loosely bent and the second bending portion 32 is made to be loosely bent in the first direction X1, it is easy to insert the rigid portion D12 of the treatment tool D10 into the channel 11 formed in the first bending portion 31 while preventing the treatment target P1 from shifting out of the angle $\theta$ of view of the observation unit 17.

When the position detection portion 79 identifies that the position of the distal end of the rigid portion D12 is positioned at the distal end of the channel 11 formed in the straight tube portion 34 (the first bending portion 31) and the second bending detection portion 72a detects that the radius of curvature of the axis C2 of the channel 11 formed in the second bending portion 32 is smaller than the predetermined value, the control portion 132 performs the following processing.

Figure 27:
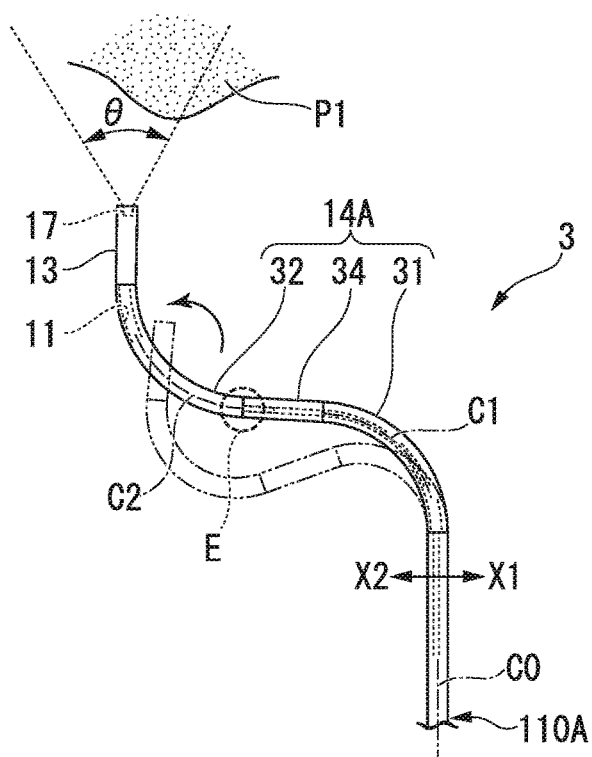
FIG. 27 is a view showing the action of the endoscope device according to the third embodiment of the invention.
Figure 28:
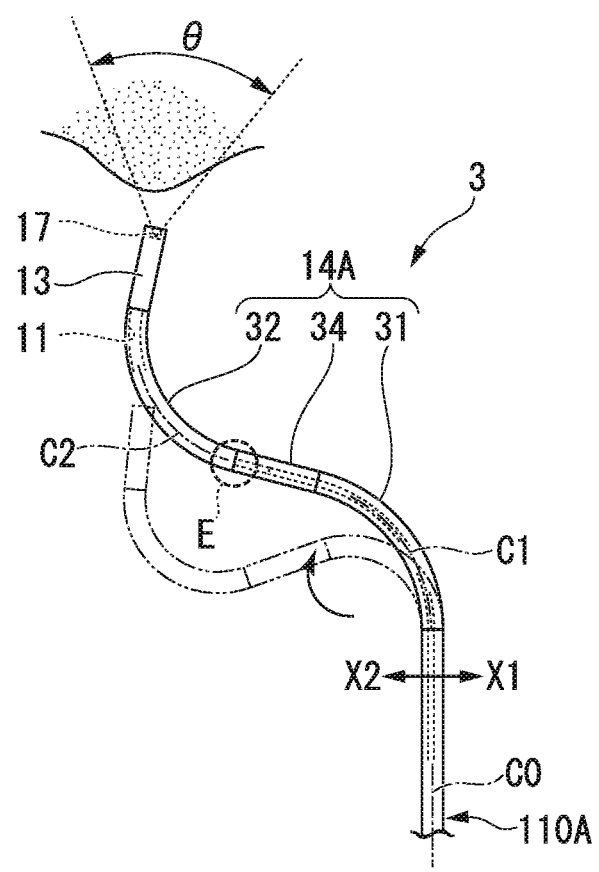
FIG. 28 is a view showing the action of the endoscope device according to the third embodiment of the invention.

That is, the control portion 132 releases the holding of the second operation-main wire 42a, which is performed by the second wire drive motor 53, and moves the second operation-auxiliary wire 112a to the proximal end side by the second auxiliary wire drive motor 123. Accordingly, the control portion 132 makes the radius of curvature of the axis C2 of the channel 11, which is formed in the second bending portion 32, be equal to or larger than the predetermined value and makes the second bending portion 32 to be loosely bent in the first direction X1 as shown in FIG. 27.

However, there is a possibility that the treatment target P1 may deviate from the angle $\theta$ of view of the observation unit 17 when the second bending portion 32 is merely made to be loosely bent in the first direction X1.

Accordingly, the control portion 132 makes the first bending portion 31 in the second direction X2 from the axis C0 to be loosely bent, while makes the second bending portion 32 to be loosely bent in the first direction X1 y, releasing the holding of the first operation-auxiliary wire 111a that is performed by the first auxiliary wire drive motor 122 and moving the first operation-main wire 41a to the proximal end side by the first wire drive motor 52.

When the second bending portion 32 is made to be loosely bent in the first direction X1 while the first bending portion 31 in the second direction X2 is made to be loosely bent, it is easy to insert the rigid portion D12 of the treatment tool D10 into the channel 11 formed in the second bending portion 32 while preventing the treatment target P1 from shifting out of the angle $\theta$ of view of the observation unit 17.

The first to third embodiments of the invention have been described above in detail with reference to the drawings. However, the specific structures of the invention are not limited to the embodiments and may include modifications, combinations, elimination, and the like of structures without departing from the gist of the invention. In addition, it goes without saying that the structures described in the respective embodiments can be appropriately combined and used.

For example, the multi-stage bending portion has been adapted to include three bending portions 31 to 33 in the first and second embodiments. However, the number of the bending portions of the multi-stage bending portion is not limited thereto, and may be two or four or more. Even in the third embodiment, the number of the bending portions of the multi-stage bending portion may be three or more.

An example in which the bending portions 31 to 33 and the angle knob are not connected to each other by the operation wires has been described in each of the embodiments. However, the bending portions 31 to 33 and the angle knob may be connected to each other through a clutch by an operation wires. In this case, when a control mode is the automatic operation mode, the connection between the bending portions 31 to 33 and the angle knob is released by the clutch.

A structure in which the rigid portion D12 is provided at the distal end portion of the treatment tool D10 in the longitudinal direction has been described in each of the embodiments, but the rigid portion may be provided on a middle portion of the treatment tool in the longitudinal direction.

The embodiments of the invention have been described above with reference to the drawings, but specific structures of the invention are not limited to the embodiments and may include various modifications without departing from the scope of the invention. The invention is not limited to the above-mentioned embodiments and is limited only by the accompanying claims.

What is claimed is:

1. An endoscope device comprising:
a flexible insertion portion in which a channel, into which a medical instrument is capable of being inserted, is formed;
a flexible tube portion that is disposed at a proximal end portion of the insertion portion;
a first bending portion that is disposed more distal than the flexible tube portion of the insertion portion and is bendable with respect to a distal end portion of the flexible tube portion;
a second bending portion that is disposed more distal than the first bending portion of the insertion portion and is bendable with respect to a distal end portion of the first bending portion;
an observation portion that is disposed more distal than the second bending portion of the insertion portion and configured to acquire an image on the front of the insertion portion;
a first drive portion that is configured to bend the first bending portion with respect to the distal end portion of the flexible tube portion by advancing or retracting a first operation wire which is connected to the first bending portion;
a second drive portion that is configured to bend the second bending portion with respect to the distal end portion of the first bending portion;
a position detection portion that is configured to detect that a position of a rigid distal end portion disposed at a distal end of the medical instrument moving in the channel, is a predetermined position of the channel formed in the first bending portion or in the second bending portion, and send a detection result of the position of the rigid distal end portion of the medical instrument as a first input signal when the rigid distal end portion is detected to be in the channel formed in the first bending portion or a second input signal when the rigid distal end portion is detected to be in the channel formed in the second bending portion;
a first bending detection portion that is configured to detect a radius of curvature of an axis of the channel formed in the first bending portion and a direction in which the channel formed in the first bending portion is bent when the first input signal is received;
a second bending detection portion that is configured to detect a radius of curvature of an axis of the channel formed in the second bending portion and a direction in which the channel formed in the second bending portion is bent when the first input signal is received; and
a control portion that is configured to control generating a second drive signal driving the second drive portion based on a first drive signal driving the first drive portion, and control sending the second drive signal to the second drive portion while sending the first drive signal to the first drive portion, wherein in a case where the radius of curvature of the axis of the channel formed in the first bending portion is smaller than a predetermined value when the control portion receives the first input signal, the control portion generates the first drive signal, and the control portion sends the first drive signal to the first drive portion for controlling the first drive portion to release a holding state of the first operation wire in which the radius of curvature of the axis of the channel formed in the first bending portion is smaller than the predetermined value such that the first operation wire is capable of being manually operated to cause the first bending portion to be substantially straight in accordance with a shape of the rigid distal end portion, and wherein the second drive signal is generated based on results of the calculation of the radii of curvature by the first bending detection portion and the second bending detection portion, in a case where the radius of curvature of the axis of the channel formed in the second bending portion is smaller than the predetermined value when the control portion receives the second input signal, the control portion generates the second drive signal and the control portion sends the second drive signal to the second drive portion for controlling the second drive portion to release a holding state of the second operation wire in which the radius of curvature of the axis of the channel formed in the second bending portion is smaller than the predetermined value, such that the second operation wire is capable of being manually operated to cause the second bending portion to be bent thereby the observation portion is moved to face a treatment target.

2. The endoscope device according to claim 1, wherein the second drive portion either keeps a bending state of the second bending portion, or changes the bending state of the second bending portion into a first direction with respect to an axis of the flexible tube portion such that the radius of curvature of the axis of the channel formed in the second bending portion becomes smaller, based on the second drive signal sent from the control portion,
when the first bending detection portion detects that the direction in which the channel formed in the first bending portion is bent is the first direction from the axis of the flexible tube portion and the second bending detection portion detects that the direction in which the channel formed in the second bending portion is bent is the first direction from the axis of the flexible tube portion.

3. The endoscope device according to claim 2, wherein the second drive portion operates to advance and retract a second operation wire which is connected to the second bending portion such that the second bending portion is bent with respect to the distal end portion of the first bending portion, and
wherein the first drive portion changes the bending state of the first bending portion into the first direction with respect to the axis of the flexible tube portion, based on the first drive signal sent from the control portion, such that the radius of curvature of the axis of the channel formed in the first bending portion becomes smaller, and the second drive portion releases the holding of the second operation wire based on the second drive signal sent from the control portion, when the position detection portion detects that a position of the rigid distal end portion of the medical instrument is a predetermined position in the channel formed in the first bending portion.

4. The endoscope device according to claim 1, wherein the first drive portion changes the bending state of the first bending portion based on the first drive signal sent from the control portion such that the radius of curvature of the axis of the channel formed in the first bending portion becomes larger, and the second drive portion changes the bending state of the second bending portion based on the second drive signal sent from the control portion such that the radius of curvature of the axis of the channel formed in the second bending portion becomes larger, when the second bending detection portion detects that the direction in which the channel formed in the second bending portion is bent, is a first direction with respect to an axis of the flexible tube portion, and the first bending detection portion detects that the direction in which the channel formed in the first bending portion is bent, is a second direction with respect to the axis of the flexible tube portion.

5. The endoscope device according to claim 4, wherein the first drive portion changes the bending state of the first bending portion based on the first drive signal sent from the control portion, and the second drive portion changes the bending state of the second bending portion based on the second drive signal sent from the control portion, when the position detection portion detects that the position of the rigid distal end portion of the medical instrument is a predetermined position in the channel formed in the first bending portion.

6. The endoscope device according to claim 1, wherein the control portion generates the first drive signal for controlling the first drive portion to resume the holding state of the first operation wire in which the radius of curvature of the axis of the channel formed in the first bending portion is smaller than the predetermined value, such that the first operation wire is automatically operated to cause the first bending portion to be extremely bent again in a direction opposite to a direction in which the second bending portion is bent.

* * * * *